US007244615B2

(12) United States Patent
Adair et al.

(10) Patent No.: US 7,244,615 B2
(45) Date of Patent: *Jul. 17, 2007

(54) HUMANIZED ANTIBODIES

(75) Inventors: John Robert Adair, High Wycombe (GB); Diljeet Singh Athwal, London (GB); John Spencer Emtage, Temple Marlow (GB)

(73) Assignee: Celltech R&D Limited, Slough, Berkshire (GB)

( * ) Notice: Subject to any disclaimer, the term of this patent is extended or adjusted under 35 U.S.C. 154(b) by 543 days.

This patent is subject to a terminal disclaimer.

(21) Appl. No.: 10/704,071

(22) Filed: Nov. 7, 2003

(65) Prior Publication Data

US 2004/0076627 A1 Apr. 22, 2004

Related U.S. Application Data

(63) Continuation of application No. 08/846,658, filed on May 1, 1997, which is a continuation of application No. 08/303,569, filed on Sep. 7, 1994, now Pat. No. 5,859,205, which is a continuation of application No. 07/743,329, filed on Sep. 17, 1991, now abandoned.

(30) Foreign Application Priority Data

Dec. 21, 1989 (GB) .................................. 8928874.0
Dec. 21, 1990 (WO) ..................... PCT/GB90/02017

(51) Int. Cl.
*C12P 21/00* (2006.01)
(52) U.S. Cl. ................ 435/320.1; 536/23.1; 536/23.53; 435/71.1; 530/387.3; 530/387.1; 530/388.22; 424/133.1; 424/143.1
(58) Field of Classification Search ............... 536/23.1, 536/23.53; 435/320.1, 71.1; 530/387.3, 530/387.1, 388.22; 424/133.1, 143.1, 134.1
See application file for complete search history.

(56) References Cited

U.S. PATENT DOCUMENTS

| 4,348,376 | A |   | 9/1982  | Goldenberg |             |
|-----------|---|---|---------|------------|-------------|
| 4,816,567 | A | * | 3/1989  | Cabilly et al. | ............ 530/387.3 |
| 5,530,101 | A |   | 6/1996  | Queen et al. |           |
| 5,585,089 | A |   | 12/1996 | Queen et al. |           |
| 5,618,920 | A | * | 4/1997  | Robinson et al. | ........ 530/387.1 |
| 5,693,761 | A |   | 12/1997 | Queen et al. |           |
| 5,693,762 | A | * | 12/1997 | Queen et al. | ............ 530/387.3 |
| 6,180,370 | B1 |  | 1/2001  | Queen et al. |           |

FOREIGN PATENT DOCUMENTS

| EP | 0 239 400 A2 | 9/1987 |
| EP | 0 323 806 A1 | 7/1989 |
| EP | 0 328 404 A1 | 8/1989 |
| EP | 0 365 209 A2 | 4/1990 |
| EP | 0 403 156 A1 | 12/1990 |
| EP | 0 451 216 B1 | 10/1991 |
| EP | 0 682 040 B1 | 11/1995 |
| WO | WO 89/07452 | 8/1989 |
| WO | WO 90/07861 | 7/1990 |
| WO | WO 92/04381 | 3/1992 |
| WO | WO 92/11018 | 7/1992 |
| WO | WO 92/15683 | 9/1992 |
| WO | WO 92/16553 | 10/1992 |

OTHER PUBLICATIONS

Chothia, Cyrus and Lesk, Arthur M., "Canonical Structures for the Hypervariable Regions of Immunoglobulins" *J. Mol. Biol.*, 196:901-917, (1987) (pp. 901 and 904).
Chothia, Cyrus, et al., "Conformations of Immunoglobulin hypervariable regions," *Nature*, 342:877-883, (1989).
Jones, Peter T., et al., "Replacing the complementarity-determining regions in a human antibody with those from a mouse," *Nature*, 321:522-525, (1986).
Queen, Cary, et al., "A humanized antibody that binds to the interleukin 2 receptor," *Proc. Natl. Acad. Sci. USA*, 86:10029-10033, (1989).
Riechmann, Lutz, et al., "Reshaping human antibodies for therapy," *Nature*, 332:323-327, (1988).
Roberts, S., et al., "Generation of an antibody with enhanced affinity and specificity for its antigen by protein engineering," *Nature*, 328:731-734, (1987).
Verhoeyen, Martine, et al., "Reshaping Human Antibodies: Grafting an Antilysozyme Activity," *Science*, 239:1534-1536 (1988).
Ward, Sally E., et al., "Binding activities of a repertoire of single immunoglobulin variable domains secreted from *Escherichia coli*," *Nature*, 341:544-546, (1989).
Chambers 20th Century Dictionary (1973 Edition), p. 1128.

* cited by examiner

*Primary Examiner*—Sheela J. Huff
*Assistant Examiner*—Parithosh K. Tungaturthi
(74) *Attorney, Agent, or Firm*—Doreen Yatko Trujillo; Cozen O'Connor, P.C.

(57) ABSTRACT

CDR-grafted antibody heavy and light chains comprise acceptor framework and donor antigen binding regions, the heavy chains comprising donor residues at at least one of positions (6, 23) and/or (24, 48) and/or (49, 71) and/or (73, 75) and/or (76) and/or (78) and (88) and/or (91). The CDR-grafted light chains comprise donor residues at at least one of positions (1) and/or (3) and (46) and/or (47) or at at least one of positons (46, 48, 58) and (71). The CDR-grafted antibodies are preferably humanized antibodies, having non human, e.g. rodent, donor and human acceptor frameworks, and may be used for in vivo therapy and diagnosis. A generally applicable protocol is disclosed for obtaining CDR-grafted antibodies.

7 Claims, 18 Drawing Sheets

```
  1 GAATTCCCAA AGACAAAatg gattttcaag tgcagatttt cagcttcctg
 51 ctaatcagtg cctcagtcat aatatccaga ggacaaattg ttctcaccca
101 gtctccagca atcatgtctg catctccagg ggagaaggtc accatgacct
151 gcagtgccag ctcaagtgta agttacatga actggtacca gcagaagtca
201 ggcacctccc ccaaaagatg gatttatgac acatccaaac tggcttctgg
251 agtccctgct cacttcaggg gcagtgggtc tgggacctct tactctctca
301 caatcagcgg catggaggct gaagatgctg ccacttatta ctgccagcag
351 tggagtagta accattcac gttcggctcg gggacaaagt tggaaataaa
401 ccgggctgat actgcaccaa ctgtatccat cttcccacca tccagtgagc
451 agttaacatc tggaggtgcc tcagtcgtgt gcttcttgaa caacttctac
501 cccaaagaca tcaatgtcaa gtggaagatt gatggcagtg aacgacaaaa
551 tggcgtcctg aacagttgga ctgatcagga cagcaaagac agcacctaca
601 gcatgagcag caccctcacg ttgaccaagg acgagtatga acgacataac
651 agctatacct gtgaggccac tcacaagaca tcaacttcac ccattgtcaa
701 gagcttcaac aggaatgagt gtTAGAGACA AAGGTCCTGA GACGCCACCA
751 CCAGCTCCCA GCTCCATCCT ATCTTCCCTT CTAAGGTCTT GGAGGCTTCC
801 CCACAAGCGC tTACCACTGT TGCGGTGCTC TAAACCTCCT CCCACCTCCT
851 TCTCCTCCTC CTCCCTTTCC TTGGCTTTTA TCATGCTAAT ATTTGCAGAA
901 AATATTCAAT AAAGTGAGTC TTTGCCTTGA AAAAAAAAAA AAA
(SEQ ID NO:4)
```

FIG. 1a

```
  1 MDFQVQIFSF LLISASVIIS RGDQIVLTQSP AIMSASPGEK VTMTCSASSS
 51 VSYMNWYQQK SGTSPKRWIY DTSKLASGVP AHFRGSGSGT SYSLTISGME
101 AEDAATYYCQ QWSSNPFTFG SGTKLEINRA DTAPTVSIFP PSSEQLTSGG
151 ASVVCFLNNF YPKDINVKWK IDGSERQNGV LNSWTDQDSK DSTYSMSSTL
201 TLTKDEYERH NSYTCEATHK TSTSPIVKSF NRNEC* (SEQ ID NO:5)
```

FIG. 1b

```
   1  GAATTCCCCT CTCCACAGAC ACTGAAAACT CTGACTCAAC ATGGAAAGGC
  51  ACTGGATCTT TCTACTCCTG TTGTCAGTAA CTGCAGGTGT CCACTCCCAG
 101  GTCCAGCTGC AGCAGTCTGG GGCTGAACTG GCAAGACCTG GGGCCTCAGT
 151  GAAGATGTCC TGCAAGGCTT CTGGCTACAC CTTTACTAGG TACACGATGC
 201  ACTGGGTAAA ACAGAGGCCT GGACAGGGTC TGGAATGGAT TGGATACATT
 251  ATTCCTAGCC GTGGTTATAC TAATTACAAT CAGAAGTTCA AGGACAAGGC
 301  CACATTGACT ACAGACAAAT CCTCCAGCAC AGCCTACATG CAACTGAGCA
 351  GCCTGACATC TGAGGACTCT GCAGTCTATT ACTGTGCAAG ATATTATGAT
 401  GATCATTACT GCCTTGACTA CTGGGGCCAA GGCACCACTC TCACAGTCTC
 451  CTCAGCCAAA ACAACAGCCC CATCGGTCTA TCCACTGGCC CCTGTGTGTG
 501  GAGATACAAC TGGCTCCTCG GTGACTCTAG GATGCCTGGT CAAGGGTTAT
 551  TTCCCTGAGC CAGTGACCTT GACCTGGAAC TCTGGATCCC TGTCCAGTGG
 601  TGTGCACACC TTCCCAGCTG TCCTGCAGTC TGACCTCTAC ACCCTCAGCA
 651  GCTCAGTGAC TGTAACCTCG AGCACCTGGC CAGCCAGTC CATCACCTGC
 701  AATGTGGCCC ACCCGGCAAG CAGCACCAAG GTGGACAAGA AAATTGAGCC
 801  ACCTCTTGGG TGGACCATCC GTCTTCATCT TCCCTCCAAA GATCAAGGAT
 851  GTACTCATGA TCTCCCTGAG CCCCATAGTC ACATGTGTGG TGGTGGATGT
 901  GAGCGAGGAT GACCCAGATG TCCAGATCAG CTGGTTTGTG AACAACGTGG
 951  AAGTACACAC AGCTCAGACA CAAACCCATA GAGAGGATTA CAACAGTACT
1001  CTCCGGGTGG TCAGTGCCCT CCCCATCCAG CACCAGGACT GGATGAGTGG
1051  CAAGGAGTTC AAATGCAAGG TCAACAACAA AGACCTCCCA GCGCCCATCG
1101  AGAGAACCAT CTCAAAACCC AAAGGGTCAG TAAGAGCTCC ACAGGTATAT
1151  GTCTTGCCTC CACCAGAAGA AGAGATGACT AAGAAACAGG TCACTCTGAC
1201  CTGCATGGTC ACAGACTTCA TGCCTGAAGA CATTTACGTG GAGTGGACCA
1251  ACAACGGGAA AACAGAGCTA AACTACAAGA ACACTGAACC AGTCCTGGAC
1301  TCTGATGGTT CTTACTTCAT GTACAGCAAG CTGAGAGTGG AAAAGAAGAA
1351  CTGGGTGGAA AGAAATAGCT ACTCCTGTTC AGTGGTCCAC GAGGGTCTGC
1401  ACAATCACCA CACGACTAAG AGCTTCTCCC GGACTCCGGG TAAATGAGCT
1451  CAGCACCCAC AAAACTCTCA GGTCCAAAGA GAGACCCACA CTCATCTCCA
1501  TGCTTCCCTT GTATAAATAA AGCACCCAGC AATGCCTGGG ACCATGTAAA
1551  AAAAAAAAAA AAAGGAATTC  (SEQ ID NO:6)
```

*FIG. 2a*

OKT 3 HEAVY CHAIN PROTEIN SEQUENCE DEDUCED FROM DNA SEQUENCE

```
  1   MERHWIFLLL  LSVTAGVHSQ  VQLQQSGAEL  ARPGASVKMS  CKASGYTFTR
 51   YTMHWVKQRP  GQGLEWIGYI  NPSRGYTNYN  QKFKDKATLT  TDKSSSTAYM
101   QLSSLTSEDS  AVYYCARYYD  DHYCLDYWGQ  GTTLTVSSAK  TTAPSVYPLA
151   PVCGDTTGSS  VTLGCLVKGY  FPEPVTLTWN  SGSLSSGVHT  FPAVLQSDLY
201   TLSSSVTVTS  STWPSQSITC  NVAHPASSTK  VDKKIEPRGP  TIKPCPPCKC
251   PAPNLLGGPS  VFIFPPKIKD  VLMISLSPIV  TCVVVDVSED  DPDVQISWFV
301   NNVEVHTAQT  QTHREDYNST  LRVVSALPIQ  HQDWMSGKEF  KCKVNNKDLP
351   APIERTISKP  KGSVRAPQVY  VLPPPEEEMT  KKQVTLTCMV  TDFMPEDIYV
401   EWTNNGKTEL  NYKNTEPVLD  SDGSYFMYSK  LRVEKKNWVE  RNSYSCSVVH
451   EGLHNHHTTK  SFSRTPGK*   (SEQ ID NO:7)
```

FIG. 2b

```
                  1                     23                          42
                  NN         N           N              N    N
RES TYPE      SBspSPESssBSbSsSssPSPSPsPSsse*s*p*Pi^ISsSe
Okt3vl        QIVLTQSPAIMSASPGEKVTMTCSASS.SVSYMNWYQQKSGT
REI           DIQMTQSPSSLSASVGDRVTITCQASQDIIKYLNWYQQIPGK
                                          ? ?
              CDR1    (LOOP)              *******
              CDR1    (KABAT)             **********

56                                  85
              N  NN
RES TYPE      *IsiPpleesesssSBEsePsPSBSSEsPspsPsseesSPePb
Okt3vl        SPKRWIYDTSKLASGVPAHFRGSGSGTSYSLTISGMEAEDAAT
REI           APKLLIYEASNLQAGVPSRFSGSGSGTDYTFTISSLQPEDIAT   (SEQ
ID NO:8)
                ?  ??                                   ?   ?
                   *******  CDR2 (LOOP/KABAT)

102   108
RES TYPE      PiPIPies**iPIIsPPSPSPSS
Okt3vl        YYCQQWSSNPFTFGSGTKLEINR   (SEQ ID NO:29)
REIvl         YYCQQYQSLPYTFGQGTKLQIIR   (SEQ ID NO:9)
                                 ?  ?
                  ******         CDR3  (LOOP)
                  *********      CRD3(KABAT)
```

*FIG. 3*

```
                NN N                       23 26      32 35  N39   43
RES TYPE    SESPs^SBssS^sSSsSpSpSPsPSEbSBssBePi^PIpiesss
Okt3h       QVQLQQSGAELARPGASVKMSCKASGYTFTRYTMNHWVKQRPGQ
KOL         QVQLVESGGGVVQPGRSLRLSCSSSGFIFSSYAMYWVRQAPGK
                 ?                          ??
                                                  ******    CDR1  (LOOP)
                                                   *****    CDR1  (KABAT)

52a    60       65     N N  N     82abc         89
RES TYPE    IIeIppp^sssssssss^ps^pSSsbSpseSsSseSp^pSpsSBssS^ePb
Okt3vh      GLEWIGYINPSRGYTNTNQKFKRKATLTTDKSSSTAYMQLSSLTSEDSAV
KOL         GLEWVAIIWDDGSDQHYADSVKGRFTISRDNSKNTLFLQMDSLPPEDTGV
                 ??                          ? ? ? ?                 ?
                 ************   CDR2  (LOOP)
              ******************  CDR2  (KABAT)

92 N                    107     113
RES TYPE    PiPIEisssssiiisssbibi*EIPIP*spSBSS
Okt3vh      YYCARYYDDHY.......CLDYWGQGTTLTVSS    (SEQ ID NO:30)
KOL         YFCARDGGHGFCSSASCFGPDYWGQGTPVTVSS    (SEQ ID NO:10)
                ******************  CRD4  (KABAT/LOOP)
```

*FIG. 4*

OKT 3 HEAVY CHAIN CDR GRAFTS 1. gH341 and derivatives

```
              1                          26        35  39  43
Okt3vh    QVQLQQSGAELARPGASVKMSCKASGYTFTRYTMHWVKQRPGQ
gH341     QVQLVESGGGVVQDGRSLRLSCSSSGYTFTRYTMHWVRQAPGK    JA178
gH341A    QVQLVQSGGGVVQPGRSLRLSCKASGYTFTRYTMHWVRQAPGK    JA185 gH341E    QVQLVQSGGGVVQPGRSLRLSCKASGYTFTRYTMHWVRQAPGK    JA198
gH341*    QVQLVQSGGGVVQPGRSLRLSCKASGYTFTRYTMHWVRQAPGK    JA207
gH341*    QVQLVQSGGGVVQPGRSLRLSCKASGYTFTRYTMHWVRQAPGK    JA209
gH341D    QVQLVQSGGGVVQPGRSLRLSCKASGYTFTRYTMHWVRQAPGK    JA197
gH341*    QVQLVQSGGGVVQPGRSLRLSCKASGYTFTRYTMHWVRQAPGK    JA199
gH341C    QVQLVQSGGGVVQPGRSLRLSCKASGYTFTRYTMHWVRQAPGK    JA184 gH341*    QVQLVQSGGGVVQPGRSLRLSCSASGYTFTRYTMHWVRQAPGK    JA203
gH341*    QVQLVESGGGVVQPGRSLRLSCSASGYTFTRYTMHWVRQAPGK    JA205
gH341B    QVQLVESGGGVVQPGRSLRLSCSSSGYTFTRYTMHWVRQAPGK    JA183
gH341*    QVQLVQSGGGVVQPGRSLRLSCSASGYTFTRYTMHWVRQAPGK    JA204
gH341*    QVQLVESGGGVVQPGRSLRLSCSASGYTFTRYTMHWVRQAPGK    JA206
gH341*    QVQLVQSGGGVVQPGRSLRLSCSASGYTFTRYTMHWVRQAPGK    JA208
KOL       QVQLVESGGGVVQPGRSLRLSCSSSGFIFSSYAMYWVRQAPGK
```

FIG. 5a

```
            44     50                65                 83
Okt3vh   GLEWIGYINPSRGYTNYNQKFKDKATLTTDKSSSTAYMQLSSLT
gH341    GLEWVAYINPSRGYTNYNQKFKDRFTISRDNSKNTLFLQMDSLR    JA178
gH341A   GLEWIGYINPSRGYTNYNQKVKDRFTISTDKSKSTAFLQMDSLR    JA185 gH341E   GLEWIGYINPSRGYTNYNQKVKDRFTISTDKSKSTAFLQMDSLR    JA198
gH341*   GLEWIGYINPSRGYTNYNQKVKDRFTISTDKSKNTAFLQMDSLR    JA207
gH341*   GLEWIGYINPSRGYTNYNQKVKDRFTISRDNSKNTAFLQMDSLR    JA209
gH341D   GLEWIGYINPSRGYTNYNQKVKDRFTISTDKSKNTLFLQMDSLR    JA197
gH341*   GLEWIGYINPSRGYTNYNQKVKDRFTISRDNSKNTLFLQMDSLR    JA199
gH341C   GLEWVAYINPSRGYTNYNQKFKDRFTISRDNSKNTLFLQMDSLR    JA184 gH341*   GLEWIGYINPSRGYTNYNQKVKDRFTISTDKSKSTAFLQMDSLR    JA207
gH341*   GLEWIGYINPSRGYTNYNQKVKDRFTISTDKSKSTAFLQMDSLR    JA205
gH341B   GLEWIGYINPSRGYTNYNQKVKDRFTISTDKSKSTAFLQMDSLR    JA183
gH341*   GLEWIGYINPSRGYTNYNQKVKDRFTISTDKSKSTAFLQMDSLR    JA204
gH341*   GLEWIGYINPSRGYTNYNQKVKDRFTISTDKSKSTAFLQMDSLR    JA206
gH341*   GLEWIGYINPSRGYTNYNQKVKDRFTISTDKSKNTAFLQMDSLR    JA208
KOL      GLEWVAIIWDDGSDQHYADSVKGRFTISRDNSKNTLFLQMDSLR
```

*FIG. 5b*

```
         84        95       102      113              SEQ ID NO:
Okt3vh   SEDSAVYYCARYYDDHY.......CLDYWGQGTTLTVSS              30
gH341    PEDTGVYFCARYYDDHY.......CLDYWGQGTTLTVSS    JA178     11
gH341A   PEDTAVYYCARYYDDHY.......CLDYWGQGTTLTVSS    JA185     12 gH341E   PEDTGVYFCARYYDDHY.......CLDYWGQGTTLTVSS    JA198     13
gH341*   PEDTGVYFCARYYDDHY.......CLDYWGQGTTLTVSS    JA207     14
gH341D   PEDTGVYFCARYYDDHY.......CLDYWGQGTTLTVSS    JA197     15
gH341*   PEDTGVYFCARYYDDHY.......CLDYWGQGTTLTVSS    JA209     16
gH341*   PEDTGVYFCARYYDDHY.......CLDYWGQGTTLTVSS    JA199     17
gH341C   PEDTGVYFCARYYDDHY.......CLDYWGQGTTLTVSS    JA184     18 gH341*   PEDTAVYYCARYYDDHY.......CLDYWGQGTTLTVSS    JA203     19
gH341*   PEDTAVYYCARYYDDHY.......CLDYWGQGTTLTVSS    JA205     20
gH341B   PEDTAVYYCARYYDDHY.......CLDYWGQGTTLTVSS    JA183     21
gH341*   PEDTGVYFCARYYDDHY.......CLDYWGQGTTLTVSS    JA204     22
gH341*   PEDTGVYFCARYYDDHY.......CLDYWGQGTTLTVSS    JA206     23
gH341*   PEDTGVYFCARYYDDHY.......CLDYWGQGTTLTVSS    JA208     24
KOL      PEDTGVYFCARDGGHGFCSSASCFGPDYWGQGTPVTVSS              10
```

*FIG. 5c*

OKT3 LIGHT CHAIN CDR GRAFTING 1. gL221 and derivatives

```
            1                        24        34        42
Okt3vl  QIVLTQSPAQMSASPGEKVTMTCSASS.SVSYMNWYQQKSGT
gL221   DIQMTQSPSSLSASVGDRVTITCSASS.SVSYMNWYQQTPGK
gL221A  QIVMTQSPSSLSASVGDRVTITCSASS.SVSYMNWYQQTPGK
gL221B  QIVMTQSPSSLSASVGDRVTITCSASS.SVSYMNWYQQTPGK
gL221C  DIQMTQSPSSLSASVGDRVTITCSASS.SVSYMNWYQQTPGK
REI     DIQMTQSPSSLSASVGDRVTITCQASQDIIKYLNWYQQTPGK 43    50    56                           85
Okt3vl  SPKRWIYDTSKLASGVPAHFRGSGSGTSYSLTISGMEAEDAAT
gL221   APKLLIYDTSKLASGVPSRFSGSGSGTDYTFTISSLQPEDIAT
gL221A  APKRWIYDTSKLASGVPSRFSGSGSGTDYTFTISSLQPEDIAT
gL221B  APKLLIYDTSKLASGVPSRFSGSGSGTDYTFTISSLQPEDIAT
gL221C  APKRWIYDTSKLASGVPSRFSGSGSGTDYTFTISSLQPEDIAT
REI     APKLLIYEASNLQAGVPSRFSGSGSGTDYTFTISSLQPEDIAT  (SEQ ID NO:8)

86  91   96        108
Okt3vl  YYCQQWSSNPFTFGSGTKLEINR      (SEQ ID NO:29)
gL221   YYCQQWSSNPETFGQGTKLQITR      (SEQ ID NO:25)
gL221A  YYCQQWSSNPETFGQGTKLQITR      (SEQ ID NO:26)
gL221B  YYCQQWSSNPETFGQGTKLQITR      (SEQ ID NO:27)
gL221C  YYCQQWSSNPETFGQGTKLQITR      (SEQ ID NO:28)
REI     YYCQQYQSLPYTFGQGTKLQITR      (SEQ ID NO:9)
```

CDR'S ARE UNDERLINED

FRAMEWORK RESIDUES INCLUDED IN THE GENE ARE DOUBLE UNDERLINED

*FIG. 6*

SEQUENCE LISTING (1) GENERAL INFORMATION:

(iii) NUMBER OF SEQUENCES: 30

(2) INFORMATION FOR SEQ ID NO: 1:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO: 1:

TCCAGATGTT AACTGCTCAC                                                    20

(2) INFORMATION FOR SEQ ID NO: 2:

(i) SEQUENCE CHARACTERISTICS:
      (A) LENGTH: 23 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO: 2:

CAGGGGCCAG TGGATGGATA GAC                                           23

(2) INFORMATION FOR SEQ ID NO: 3:

(i) SEQUENCE CHARACTERISTICS:
      (A) LENGTH: 9 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO: 3:

Leu Glu Ile Asn Arg Thr Val Ala Ala
1              5

(2) INFORMATION FOR SEQ ID NO: 4:

(i) SEQUENCE CHARACTERISTICS:
      (A) LENGTH: 943 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 18..722

(ix) FEATURE:
      (A) NAME/KEY: mat_peptide
      (B) LOCATION: 84..722

(xi) SEQUENCE DESCRIPTION: SEQ ID NO: 4:

GAATTCCCAA AGACAAA ATG GAT TTT CAA GTG CAG ATT TTC AGC TTC CTG     50
                   Met Asp Phe Gln Val Gln Ile Phe Ser Phe Leu
                   -22     -20                   -15

CTA ATC AGT GCC TCA GTC ATA ATA TCC AGA GGA CAA ATT GTT CTC ACC     98

```

Leu Ile Ser Ala Ser Val Ile Ile Ser Arg Gly Gln Ile Val Leu Thr
    -10                 -5                  1               5

CAG TCT CCA GCA ATC ATG TCT GCA TCT CCA GGG GAG AAG GTC ACC ATG    146
Gln Ser Pro Ala Ile Met Ser Ala Ser Pro Gly Glu Lys Val Thr Met
            10                  15                  20

ACC TGC AGT GCC AGC TCA AGT GTA AGT TAC ATG AAC TGG TAC CAG CAG    194
Thr Cys Ser Ala Ser Ser Ser Val Ser Tyr Met Asn Trp Tyr Gln Gln
                25                  30                  35

AAG TCA GGC ACC TCC CCC AAA AGA TGG ATT TAT GAC ACA TCC AAA CTG    242
Lys Ser Gly Thr Ser Pro Lys Arg Trp Ile Tyr Asp Thr Ser Lys Leu
            40                  45                  50

GCT TCT GGA GTC CCT GCT CAC TTC AGG GGC AGT GGG TCT GGG ACC TCT    290
Ala Ser Gly Val Pro Ala His Phe Arg Gly Ser Gly Ser Gly Thr Ser
    55                  60                  65

TAC TCT CTC ACA ATC AGC GGC ATG GAG GCT GAA GAT GCT GCC ACT TAT    338
Tyr Ser Leu Thr Ile Ser Gly Met Glu Ala Glu Asp Ala Ala Thr Tyr
70                  75                  80                  85

TAC TGC CAG CAG TGG AGT AGT AAC CCA TTC ACG TTC GGC TCG GGG ACA    386
Tyr Cys Gln Gln Trp Ser Ser Asn Pro Phe Thr Phe Gly Ser Gly Thr
                90                  95                  100

AAG TTG GAA ATA AAC CGG GCT GAT ACT GCA CCA ACT GTA TCC ATC TTC    434
Lys Leu Glu Ile Asn Arg Ala Asp Thr Ala Pro Thr Val Ser Ile Phe
            105                 110                 115

CCA CCA TCC AGT GAG CAG TTA ACA TCT GGA GGT GCC TCA GTC GTG TGC    482
Pro Pro Ser Ser Glu Gln Leu Thr Ser Gly Gly Ala Ser Val Val Cys
    120                 125                 130

TTC TTG AAC AAC TTC TAC CCC AAA GAC ATC AAT GTC AAG TGG AAG ATT    530
Phe Leu Asn Asn Phe Tyr Pro Lys Asp Ile Asn Val Lys Trp Lys Ile
135                 140                 145

GAT GGC AGT GAA CGA CAA AAT GGC GTC CTG AAC AGT TGG ACT GAT CAG    578
Asp Gly Ser Glu Arg Gln Asn Gly Val Leu Asn Ser Trp Thr Asp Gln
150                 155                 160                 165

GAC AGC AAA GAC AGC ACC TAC AGC ATG AGC AGC ACC CTC ACG TTG ACC    626
Asp Ser Lys Asp Ser Thr Tyr Ser Met Ser Ser Thr Leu Thr Leu Thr
            170                 175                 180

AAG GAC GAG TAT GAA CGA CAT AAC AGC TAT ACC TGT GAG GCC ACT CAC    674
Lys Asp Glu Tyr Glu Arg His Asn Ser Tyr Thr Cys Glu Ala Thr His
    185                 190                 195

AAG ACA TCA ACT TCA CCC ATT GTC AAG AGC TTC AAC AGG AAT GAG TGT    722
Lys Thr Ser Thr Ser Pro Ile Val Lys Ser Phe Asn Arg Asn Glu Cys
200                 205                 210

TAGAGACAAA GGTCCTGAGA CGCCACCACC AGCTCCCAGC TCCATCCTAT CTTCCCTTCT    782

AAGGTCTTGG AGGCTTCCCC ACAAGCGCTT ACCACTGTTG CGGTGCTCTA AACCTCCTCC    842

CACCTCCTTC TCCTCCTCCT CCCTTTCCTT GGCTTTTATC ATGCTAATAT TTGCAGAAAA    902

TATTCAATAA AGTGAGTCTT TGCCTTGAAA AAAAAAAAA A                         943
```

(2) INFORMATION FOR SEQ ID NO: 5:

(i) SEQUENCE CHARACTERISTICS:
        (A) LENGTH: 235 amino acids
        (B) TYPE: amino acid
        (D) TOPOLOGY: linear (ii) MOLECULE TYPE: protein (xi) SEQUENCE DESCRIPTION: SEQ ID NO: 5:

```
Met Asp Phe Gln Val Gln Ile Phe Ser Phe Leu Leu Ile Ser Ala Ser
-22         -20                 -15                 -10

Val Ile Ile Ser Arg Gly Gln Ile Val Leu Thr Gln Ser Pro Ala Ile
```

```
              -5              1              5              10
        Met Ser Ala Ser Pro Gly Glu Lys Val Thr Met Thr Cys Ser Ala Ser
                        15              20              25

Ser Ser Val Ser Tyr Met Asn Trp Tyr Gln Gln Lys Ser Gly Thr Ser
                    30              35              40

Pro Lys Arg Trp Ile Tyr Asp Thr Ser Lys Leu Ala Ser Gly Val Pro
                    45              50              55

Ala His Phe Arg Gly Ser Gly Ser Gly Thr Ser Tyr Ser Leu Thr Ile
                60              65              70

Ser Gly Met Glu Ala Glu Asp Ala Ala Thr Tyr Tyr Cys Gln Gln Trp
        75              80              85              90

Ser Ser Asn Pro Phe Thr Phe Gly Ser Gly Thr Lys Leu Glu Ile Asn
                        95              100             105

Arg Ala Asp Thr Ala Pro Thr Val Ser Ile Phe Pro Pro Ser Ser Glu
                    110             115             120

Gln Leu Thr Ser Gly Gly Ala Ser Val Val Cys Phe Leu Asn Asn Phe
                    125             130             135

Tyr Pro Lys Asp Ile Asn Val Lys Trp Lys Ile Asp Gly Ser Glu Arg
                140             145             150

Gln Asn Gly Val Leu Asn Ser Trp Thr Asp Gln Asp Ser Lys Asp Ser
        155             160             165             170

Thr Tyr Ser Met Ser Ser Thr Leu Thr Leu Thr Lys Asp Glu Tyr Glu
                        175             180             185

Arg His Asn Ser Tyr Thr Cys Glu Ala Thr His Lys Thr Ser Thr Ser
                    190             195             200

Pro Ile Val Lys Ser Phe Asn Arg Asn Glu Cys
                    205             210

(2) INFORMATION FOR SEQ ID NO: 6:

(i) SEQUENCE CHARACTERISTICS:
        (A) LENGTH: 1570 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 41..1444

(ix) FEATURE:
        (A) NAME/KEY: mat_peptide
        (B) LOCATION: 98..1444

(xi) SEQUENCE DESCRIPTION: SEQ ID NO: 6:

GAATTCCCCT CTCCACAGAC ACTGAAAACT CTGACTCAAC ATG GAA AGG CAC TGG           55
                                            Met Glu Arg His Trp
                                            -19             -15

ATC TTT CTA CTC CTG TTG TCA GTA ACT GCA GGT GTC CAC TCC CAG GTC          103
Ile Phe Leu Leu Leu Leu Ser Val Thr Ala Gly Val His Ser Gln Val
            -10                 -5                  1

CAG CTG CAG CAG TCT GGG GCT GAA CTG GCA AGA CCT GGG GCC TCA GTG          151
Gln Leu Gln Gln Ser Gly Ala Glu Leu Ala Arg Pro Gly Ala Ser Val
        5               10              15

AAG ATG TCC TGC AAG GCT TCT GGC TAC ACC TTT ACT AGG TAC ACG ATG          199
Lys Met Ser Cys Lys Ala Ser Gly Tyr Thr Phe Thr Arg Tyr Thr Met
    20              25              30

CAC TGG GTA AAA CAG AGG CCT GGA CAG GGT CTG GAA TGG ATT GGA TAC          247
```

|        |        |        |        |        |        |        |        |        |        |        |        |        |        |        |        |      |
|--------|--------|--------|--------|--------|--------|--------|--------|--------|--------|--------|--------|--------|--------|--------|--------|------|
|        |        |        |        |        |        |        |        |        |        |        |        |        |        |        |        |      |

```
His Trp Val Lys Gln Arg Pro Gly Gln Gly Leu Glu Trp Ile Gly Tyr
 35                  40                      45                  50

ATT AAT CCT AGC CGT GGT TAT ACT AAT TAC ATT CAG AAG TTC AAG GAC      295
Ile Asn Pro Ser Arg Gly Tyr Thr Asn Tyr Ile Gln Lys Phe Lys Asp
                 55                      60                  65

AAG GCC ACA TTG ACT ACA GAC AAA TCC TCC AGC ACA GCC TAC ATG CAA      343
Lys Ala Thr Leu Thr Thr Asp Lys Ser Ser Ser Thr Ala Tyr Met Gln
                 70                      75                  80

CTG AGC AGC CTG ACA TCT GAG GAC TCT GCA GTC TAT TAC TGT GCA AGA      391
Leu Ser Ser Leu Thr Ser Glu Asp Ser Ala Val Tyr Tyr Cys Ala Arg
                 85                      90                  95

TAT TAT GAT GAT CAT TAC TGC CTT GAC TAC TGG GGC CAA GGC ACC ACT      439
Tyr Tyr Asp Asp His Tyr Cys Leu Asp Tyr Trp Gly Gln Gly Thr Thr
                100                     105                 110

CTC ACA GTC TCC TCA GCC AAA ACA ACA GCC CCA TCG GTC TAT CCA CTG      487
Leu Thr Val Ser Ser Ala Lys Thr Thr Ala Pro Ser Val Tyr Pro Leu
115                 120                     125                 130

GCC CCT GTG TGT GGA GAT ACA ACT GGC TCC TCG GTG ACT CTA GGA TGC      535
Ala Pro Val Cys Gly Asp Thr Thr Gly Ser Ser Val Thr Leu Gly Cys
                135                     140                 145

CTG GTC AAG GGT TAT TTC CCT GAG CCA GTG ACC TTG ACC TGG AAC TCT      583
Leu Val Lys Gly Tyr Phe Pro Glu Pro Val Thr Leu Thr Trp Asn Ser
                150                     155                 160

GGA TCC CTG TCC AGT GGT GTG CAC ACC TTC CCA GCT GTC CTG CAG TCT      631
Gly Ser Leu Ser Ser Gly Val His Thr Phe Pro Ala Val Leu Gln Ser
                165                     170                 175

GAC CTC TAC ACC CTC AGC AGC TCA GTG ACT GTA ACC TCG AGC ACC TGG      679
Asp Leu Tyr Thr Leu Ser Ser Ser Val Thr Val Thr Ser Ser Thr Trp
180                 185                     190

CCC AGC CAG TCC ATC ACC TGC AAT GTG GCC CAC CCG GCA AGC AGC ACC      727
Pro Ser Gln Ser Ile Thr Cys Asn Val Ala His Pro Ala Ser Ser Thr
195                 200                     205                 210

AAG GTG GAC AAG AAA ATT GAG CCC AGA GGG CCC ACA ATC AAG CCC TGT      775
Lys Val Asp Lys Lys Ile Glu Pro Arg Gly Pro Thr Ile Lys Pro Cys
                215                     220                 225

CCT CCA TGC AAA TGC CCA GCA CCT AAC CTC TTG GGT GGA CCA TCC GTC      823
Pro Pro Cys Lys Cys Pro Ala Pro Asn Leu Leu Gly Gly Pro Ser Val
                230                     235                 240

TTC ATC TTC CCT CCA AAG ATC AAG GAT GTA CTC ATG ATC TCC CTG AGC      871
Phe Ile Phe Pro Pro Lys Ile Lys Asp Val Leu Met Ile Ser Leu Ser
                245                     250                 255

CCC ATA GTC ACA TGT GTG GTG GTG GAT GTG AGC GAG GAT GAC CCA GAT      919
Pro Ile Val Thr Cys Val Val Val Asp Val Ser Glu Asp Asp Pro Asp
260                 265                     270

GTC CAG ATC AGC TGG TTT GTG AAC AAC GTG GAA GTA CAC ACA GCT CAG      967
Val Gln Ile Ser Trp Phe Val Asn Asn Val Glu Val His Thr Ala Gln
275                 280                     285                 290

ACA CAA ACC CAT AGA GAG GAT TAC AAC AGT ACT CTC CGG GTG GTC AGT     1015
Thr Gln Thr His Arg Glu Asp Tyr Asn Ser Thr Leu Arg Val Val Ser
                295                     300                 305

GCC CTC CCC ATC CAG CAC CAG GAC TGG ATG AGT GGC AAG GAG TTC AAA     1063
Ala Leu Pro Ile Gln His Gln Asp Trp Met Ser Gly Lys Glu Phe Lys
                310                     315                 320

TGC AAG GTC AAC AAC AAA GAC CTC CCA GCG CCC ATC GAG AGA ACC ATC     1111
Cys Lys Val Asn Asn Lys Asp Leu Pro Ala Pro Ile Glu Arg Thr Ile
                325                     330                 335

TCA AAA CCC AAA GGG TCA GTA AGA GCT CCA CAG GTA TAT GTC TTG CCT     1159
Ser Lys Pro Lys Gly Ser Val Arg Ala Pro Gln Val Tyr Val Leu Pro
                340                     345                 350
```

-continued

```
CCA CCA GAA GAA GAG ATG ACT AAG AAA CAG GTC ACT CTG ACC TGC ATG      1207
Pro Pro Glu Glu Glu Met Thr Lys Lys Gln Val Thr Leu Thr Cys Met
355             360                 365                 370

GTC ACA GAC TTC ATG CCT GAA GAC ATT TAC GTG GAG TGG ACC AAC AAC      1255
Val Thr Asp Phe Met Pro Glu Asp Ile Tyr Val Glu Trp Thr Asn Asn
                375                 380                 385

GGG AAA ACA GAG CTA AAC TAC AAG AAC ACT GAA CCA GTC CTG GAC TCT      1303
Gly Lys Thr Glu Leu Asn Tyr Lys Asn Thr Glu Pro Val Leu Asp Ser
            390                 395                 400

GAT GGT TCT TAC TTC ATG TAC AGC AAG CTG AGA GTG GAA AAG AAG AAC      1351
Asp Gly Ser Tyr Phe Met Tyr Ser Lys Leu Arg Val Glu Lys Lys Asn
                405                 410                 415

TGG GTG GAA AGA AAT AGC TAC TCC TGT TCA GTG GTC CAC GAG GGT CTG      1399
Trp Val Glu Arg Asn Ser Tyr Ser Cys Ser Val Val His Glu Gly Leu
            420                 425                 430

CAC AAT CAC CAC ACG ACT AAG AGC TTC TCC CGG ACT CCG GGT AAA          1444
His Asn His His Thr Thr Lys Ser Phe Ser Arg Thr Pro Gly Lys
435                 440                 445

TGAGCTCAGC ACCCACAAAA CTCTCAGGTC CAAAGAGACA CCCACACTCA TCTCCATGCT    1504

TCCCTTGTAT AAATAAAGCA CCCAGCAATG CCTGGGACCA TGTAAAAAAA AAAAAAAAAG    1564

GAATTC                                                               1570
```

(2) INFORMATION FOR SEQ ID NO: 7:

(i) SEQUENCE CHARACTERISTICS:
        (A) LENGTH: 468 amino acids
        (B) TYPE: amino acid
        (D) TOPOLOGY: linear (ii) MOLECULE TYPE: protein (xi) SEQUENCE DESCRIPTION: SEQ ID NO: 7:

```
Met Glu Arg His Trp Ile Phe Leu Leu Leu Ser Val Thr Ala Gly
-19             -15                 -10                 -5

Val His Ser Gln Val Gln Leu Gln Gln Ser Gly Ala Glu Leu Ala Arg
  1               5                  10

Pro Gly Ala Ser Val Lys Met Ser Cys Lys Ala Ser Gly Tyr Thr Phe
 15                 20                  25

Thr Arg Tyr Thr Met His Trp Val Lys Gln Arg Pro Gly Gln Gly Leu
30                  35                  40                  45

Glu Trp Ile Gly Tyr Ile Asn Pro Ser Arg Gly Tyr Thr Asn Tyr Asn
                50                  55                  60

Gln Lys Phe Lys Asp Lys Ala Thr Leu Thr Thr Asp Lys Ser Ser Ser
            65                  70                  75

Thr Ala Tyr Met Gln Leu Ser Ser Leu Thr Ser Glu Asp Ser Ala Val
                80                  85                  90

Tyr Tyr Cys Ala Arg Tyr Tyr Asp Asp His Tyr Cys Leu Asp Tyr Trp
 95                 100                 105

Gly Gln Gly Thr Thr Leu Thr Val Ser Ser Ala Lys Thr Thr Ala Pro
110                 115                 120                 125

Ser Val Tyr Pro Leu Ala Pro Val Cys Gly Asp Thr Thr Gly Ser Ser
                130                 135                 140

Val Thr Leu Gly Cys Leu Val Lys Gly Thr Phe Pro Glu Pro Val Thr
            145                 150                 155

Leu Thr Trp Asn Ser Gly Ser Leu Ser Ser Gly Val His Thr Phe Pro
            160                 165                 170

Ala Val Leu Gln Ser Asp Leu Tyr Thr Leu Ser Ser Ser Val Thr Val
```

-continued

```
            175                 180                 185
Thr Ser Ser Thr Trp Pro Ser Gln Ser Ile Thr Cys Asn Val Ala His
190                 195                 200                 205

Pro Ala Ser Ser Thr Lys Val Asp Lys Lys Ile Glu Pro Arg Gly Pro
                210                 215                 220

Thr Ile Lys Pro Cys Pro Pro Cys Lys Cys Pro Ala Pro Asn Leu Leu
                225                 230                 235

Gly Gly Pro Ser Val Phe Ile Phe Pro Pro Lys Ile Lys Asp Val Leu
                240                 245                 250

Met Ile Ser Leu Ser Pro Ile Val Thr Cys Val Val Asp Val Ser
255                 260                 265

Glu Asp Asp Pro Asp Val Gln Ile Ser Trp Phe Val Asn Asn Val Glu
270                 275                 280                 285

Val His Thr Ala Gln Thr Gln Thr His Arg Glu Asp Tyr Asn Ser Thr
                290                 295                 300

Leu Arg Val Val Ser Ala Leu Pro Ile Gln His Gln Asp Trp Met Ser
                305                 310                 315

Gly Lys Glu Phe Lys Cys Lys Val Asn Asn Lys Asp Leu Pro Ala Pro
                320                 325                 310

Ile Glu Arg Thr Ile Ser Lys Pro Lys Gly Ser Val Arg Ala Pro Gln
                335                 340                 345

Val Tyr Val Leu Pro Pro Pro Glu Glu Glu Met Thr Lys Lys Gln Val
350                 355                 360                 365

Thr Leu Thr Cys Met Val Thr Asp Phe Met Pro Glu Asp Ile Tyr Val
                370                 375                 380

Glu Trp Thr Asn Asn Gly Lys Thr Glu Leu Asn Tyr Lys Asn Thr Glu
                385                 390                 395

Pro Val Leu Asp Ser Asp Gly Ser Tyr Phe Met Tyr Ser Lys Leu Arg
                400                 405                 410

Val Glu Lys Lys Asn Trp Val Glu Arg Asn Ser Tyr Ser Cys Ser Val
                415                 420                 425

Val His Glu Gly Leu His Asn His His Thr Thr Lys Ser Phe Ser Arg
430                 435                 440                 445

Thr Pro Gly Lys (2) INFORMATION FOR SEQ ID NO: 8:

(i) SEQUENCE CHARACTERISTICS:
        (A) LENGTH: 85 amino acids
        (B) TYPE: amino acid
        (D) TOPOLOGY: linear (ii) MOLECULE TYPE: peptide (xi) SEQUENCE DESCRIPTION: SEQ ID NO: 8:

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ile Lys Tyr
                20                  25                  30

Leu Asn Trp Tyr Gln Gln Thr Pro Gly Lys Ala Pro Lys Leu Leu Ile
            35                  40                  45

Thr Glu Ala Ser Asn Leu Gln Ala Gly Val Pro Ser Arg Phe Ser Gly
        50                  55                  60

Ser Gly Ser Gly Thr Asp Tyr Thr Phe Thr Ile Ser Ser Leu Gln Pro
65                  70                  75                  80
```

-continued

```
Glu Asp Ile Ala Thr
              85

(2) INFORMATION FOR SEQ ID NO: 9:

(i) SEQUENCE CHARACTERISTICS:
        (A) LENGTH: 23 amino acids
        (B) TYPE: amino acid
        (D) TOPOLOGY: linear (ii) MOLECULE TYPE: peptide (xi) SEQUENCE DESCRIPTION: SEQ ID NO: 9:

Tyr Tyr Cys Gln Gln Tyr Gln Ser Leu Pro Tyr Thr Phe Gly Gln Gly
1               5                  10                  15

Thr Lys Leu Gln Ile Thr Arg
            20

(2) INFORMATION FOR SEQ ID NO: 10:

(i) SEQUENCE CHARACTERISTICS:
        (A) LENGTH: 126 amino acids
        (B) TYPE: amino acid
        (D) TOPOLOGY: linear (ii) MOLECULE TYPE: peptide (xi) SEQUENCE DESCRIPTION: SEQ ID NO: 10:

Gln Val Gln Leu Val Glu Ser Gly Gly Gly Val Val Gln Pro Gly Arg
1               5                  10                  15

Ser Leu Arg Leu Ser Cys Ser Ser Gly Phe Ile Phe Ser Ser Tyr
                20                  25                  30

Ala Met Tyr Trp Val Arg Gln Ala Pro Gly Lys Gly Leu Glu Trp Val
            35                  40                  45

Ala Ile Ile Trp Asp Asp Gly Ser Asp Gln His Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asp Ser Leu Arg Pro Glu Asp Thr Gly Val Tyr Phe Cys
                85                  90                  95

Ala Arg Asp Gly Gly His Gly Phe Cys Ser Ser Ala Ser Cys Phe Gly
            100                 105                 110

Pro Asp Tyr Trp Gly Gln Gly Thr Pro Val Thr Val Ser Ser
        115                 120                 125

(2) INFORMATION FOR SEQ ID NO: 11:

(i) SEQUENCE CHARACTERISTICS:
        (A) LENGTH: 119 amino acids
        (B) TYPE: amino acid
        (D) TOPOLOGY: linear (ii) MOLECULE TYPE: peptide (xi) SEQUENCE DESCRIPTION: SEQ ID NO: 11:

Gln Val Gln Leu Val Glu Ser Gly Gly Gly Val Val Gln Pro Gly Arg
1               5                  10                  15

Ser Leu Arg Leu Ser Cys Ser Ser Gly Tyr Thr Phe Thr Arg Tyr
                20                  25                  30

Thr Met His Trp Val Arg Gln Ala Pro Gly Lys Gly Leu Glu Trp Val
            35                  40                  45

Ala Tyr Ile Asn Pro Ser Arg Gly Tyr Thr Asn Tyr Asn Gln Lys Phe
```

```
                50             55              60
Lys Asp Arg Phe Thr Ile Ser Arg Asp Asn Ser Lys Asn Thr Leu Phe
 65                  70                  75                  80

Leu Gln Met Asp Ser Leu Arg Pro Glu Asp Thr Gly Val Tyr Phe Cys
                     85                  90                  95

Ala Arg Tyr Tyr Asp Asp His Tyr Cys Leu Asp Tyr Trp Gly Gln Gly
                    100                 105                 110

Thr Thr Leu Thr Val Ser Ser
            115

(2) INFORMATION FOR SEQ ID NO: 12:

(i) SEQUENCE CHARACTERISTICS:
        (A) LENGTH: 119 amino acids
        (B) TYPE: amino acid
        (D) TOPOLOGY: linear (ii) MOLECULE TYPE: peptide (xi) SEQUENCE DESCRIPTION: SEQ ID NO: 12:

Gln Val Gln Leu Val Gln Ser Gly Gly Gly Val Val Gln Pro Gly Arg
 1               5                  10                  15

Ser Leu Arg Leu Ser Cys Lys Ala Ser Gly Tyr Thr Phe Thr Arg Tyr
                20                  25                  30

Thr Met His Trp Val Arg Gln Ala Pro Gly Lys Gly Leu Glu Trp Ile
             35                  40                  45

Gly Tyr Ile Asn Pro Ser Arg Gly Tyr Thr Asn Tyr Asn Gln Lys Val
         50                  55                  60

Lys Asp Arg Phe Thr Ile Ser Thr Asp Lys Ser Lys Ser Thr Ala Phe
 65                  70                  75                  80

Leu Gln Met Asp Ser Leu Arg Pro Glu Asp Thr Ala Val Tyr Tyr Cys
                     85                  90                  95

Ala Arg Tyr Tyr Asp Asp His Tyr Cys Leu Asp Tyr Trp Gly Gln Gly
                    100                 105                 110

Thr Thr Leu Thr Val Ser Ser
            115

(2) INFORMATION FOR SEQ ID NO: 13:

(i) SEQUENCE CHARACTERISTICS:
        (A) LENGTH: 119 amino acids
        (B) TYPE: amino acid
        (D) TOPOLOGY: linear (ii) MOLECULE TYPE: peptide (xi) SEQUENCE DESCRIPTION: SEQ ID NO: 13:

Gln Val Gln Leu Val Gln Ser Gly Gly Gly Val Val Gln Pro Gly Arg
 1               5                  10                  15

Ser Leu Arg Leu Ser Cys Lys Ala Ser Gly Tyr Thr Phe Thr Arg Tyr
                20                  25                  30

Thr Met His Trp Val Arg Gln Ala Pro Gly Lys Gly Leu Glu Trp Ile
             35                  40                  45

Gly Tyr Ile Asn Pro Ser Arg Gly Tyr Thr Asn Tyr Asn Gln Lys Val
         50                  55                  60

Lys Asp Arg Phe Thr Ile Ser Thr Asp Lys Ser Lys Ser Thr Ala Phe
 65                  70                  75                  80

Leu Gln Met Asp Ser Leu Arg Pro Glu Asp Thr Gly Val Tyr Phe Cys
                     85                  90                  95
```

Ala Arg Tyr Tyr Asp Asp His Tyr Cys Leu Asp Tyr Trp Gly Gln Gly
            100                 105                 110

Thr Thr Leu Thr Val Ser Ser
        115

(2) INFORMATION FOR SEQ ID NO: 14:

(i) SEQUENCE CHARACTERISTICS:
        (A) LENGTH: 119 amino acids
        (B) TYPE: amino acid
        (D) TOPOLOGY: linear (ii) MOLECULE TYPE: peptide (xi) SEQUENCE DESCRIPTION: SEQ ID NO: 14:

Gln Val Gln Leu Val Gln Ser Gly Gly Gly Val Val Gln Pro Gly Arg
1               5                   10                  15

Ser Leu Arg Leu Ser Cys Lys Ala Ser Gly Tyr Thr Phe Thr Arg Tyr
            20                  25                  30

Thr Met His Trp Val Arg Gln Ala Pro Gly Lys Gly Leu Glu Trp Ile
        35                  40                  45

Gly Tyr Ile Asn Pro Ser Arg Gly Tyr Thr Asn Tyr Asn Gln Lys Val
    50                  55                  60

Lys Asp Arg Phe Thr Ile Ser Thr Asp Lys Ser Lys Asn Thr Ala Phe
65                  70                  75                  80

Leu Gln Met Asp Ser Leu Arg Pro Glu Asp Thr Gly Val Tyr Phe Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser
        115

(2) INFORMATION FOR SEQ ID NO: 15:

(i) SEQUENCE CHARACTERISTICS:
        (A) LENGTH: 119 amino acids
        (B) TYPE: amino acid
        (D) TOPOLOGY: linear (ii) MOLECULE TYPE: peptide (xi) SEQUENCE DESCRIPTION: SEQ ID NO: 15:

Gln Val Gln Leu Val Gln Ser Gly Gly Gly Val Val Gln Pro Gly Arg
1               5                   10                  15

Ser Leu Arg Leu Ser Cys Lys Ala Ser Gly Tyr Thr Phe Thr Arg Tyr
            20                  25                  30

Thr Met His Trp Val Arg Gln Ala Pro Gly Lys Gly Leu Glu Trp Ile
        35                  40                  45

Gly Tyr Ile Asn Pro Ser Arg Gly Tyr Thr Asn Tyr Asn Gln Lys Val
    50                  55                  60

Lys Asp Arg Phe Thr Ile Ser Arg Asp Asn Ser Lys Asn Thr Ala Phe
65                  70                  75                  80

Leu Gln Met Asp Ser Leu Arg Pro Glu Asp Thr Gly Val Tyr Phe Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser
        115

(2) INFORMATION FOR SEQ ID NO: 16:

(i) SEQUENCE CHARACTERISTICS:
        (A) LENGTH: 119 amino acids
        (B) TYPE: amino acid
        (D) TOPOLOGY: linear (ii) MOLECULE TYPE: peptide (xi) SEQUENCE DESCRIPTION: SEQ ID NO: 16:

```
Gln Val Gln Leu Val Gln Ser Gly Gly Gly Val Val Gln Pro Gly Arg
1               5                   10                  15
Ser Leu Arg Leu Ser Cys Lys Ala Ser Gly Tyr Thr Phe Thr Arg Tyr
            20                  25                  30
Thr Met His Trp Val Arg Gln Ala Pro Cys Lys Gly Leu Glu Trp Ile
        35                  40                  45
Gly Tyr Ile Asn Pro Ser Arg Gly Tyr Thr Asn Tyr Asn Gln Lys Val
    50                  55                  60
Lys Asp Arg Phe Thr Ile Ser Thr Asp Lys Ser Lys Asn Thr Leu Phe
65                  70                  75                  80
Leu Gln Met Asp Ser Leu Arg Pro Glu Asp Thr Gly Val Tyr Phe Cys
                85                  90                  95
Ala Arg Tyr Tyr Asp Asp His Tyr Cys Leu Asp Tyr Trp Gly Gln Gly
            100                 105                 110
Thr Thr Leu Thr Val Ser Ser
            115
```

(2) INFORMATION FOR SEQ ID NO: 17:

(i) SEQUENCE CHARACTERISTICS:
        (A) LENGTH: 119 amino acids
        (B) TYPE: amino acid
        (D) TOPOLOGY: linear (ii) MOLECULE TYPE: peptide (xi) SEQUENCE DESCRIPTION: SEQ ID NO: 17:

```
Gln Val Gln Leu Val Gln Ser Gly Gly Gly Val Val Gln Pro Gly Arg
1               5                   10                  15
Ser Leu Arg Leu Ser Cys Lys Ala Ser Gly Tyr Thr Phe Thr Arg Tyr
            20                  25                  30
Thr Met His Trp Val Arg Gln Ala Pro Cys Lys Gly Leu Glu Trp Ile
        35                  40                  45
Gly Tyr Ile Asn Pro Ser Arg Gly Tyr Thr Asn Tyr Asn Gln Lys Val
    50                  55                  60
Lys Asp Arg Phe Thr Ile Ser Arg Asp Asn Ser Lys Asn Thr Leu Phe
65                  70                  75                  80
Leu Gln Met Asp Ser Leu Arg Pro Glu Asp Thr Gly Val Tyr Phe Cys
                85                  90                  95
Ala Arg Tyr Tyr Asp Asp His Tyr Cys Leu Asp Tyr Trp Gly Gln Gly
            100                 105                 110
Thr Thr Leu Thr Val Ser Ser
            115
```

(2) INFORMATION FOR SEQ ID NO: 18:

(i) SEQUENCE CHARACTERISTICS:
        (A) LENGTH: 119 amino acids
        (B) TYPE: amino acid
        (D) TOPOLOGY: linear (ii) MOLECULE TYPE: peptide (xi) SEQUENCE DESCRIPTION: SEQ ID NO: 18:

```
Gln Val Gln Leu Val Gln Ser Gly Gly Gly Val Val Gln Pro Gly Arg
1               5                   10                  15

Ser Leu Arg Leu Ser Cys Lys Ala Ser Gly Tyr Thr Phe Thr Arg Tyr
            20                  25                  30

Thr Met His Trp Val Arg Gln Ala Pro Cys Lys Gly Leu Glu Trp Val
        35                  40                  45

Ala Tyr Ile Asn Pro Ser Arg Gly Tyr Thr Asn Tyr Asn Gln Lys Val
50                  55                  60

Lys Asp Arg Phe Thr Ile Ser Thr Asp Lys Ser Lys Ser Thr Ala Phe
65                  70                  75                  80

Leu Gln Met Asp Ser Leu Arg Pro Glu Asp Thr Gly Val Tyr Phe Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser
            115
```

(2) INFORMATION FOR SEQ ID NO: 19:

(i) SEQUENCE CHARACTERISTICS:
        (A) LENGTH: 119 amino acids
        (B) TYPE: amino acid
        (D) TOPOLOGY: linear (ii) MOLECULE TYPE: peptide (xi) SEQUENCE DESCRIPTION: SEQ ID NO: 19:

```
Gln Val Gln Leu Val Gln Ser Gly Gly Gly Val Val Gln Pro Gly Arg
1               5                   10                  15

Ser Leu Arg Leu Ser Cys Ser Ala Ser Gly Tyr Thr Phe Thr Arg Tyr
            20                  25                  30

Thr Met His Trp Val Arg Gln Ala Pro Cys Lys Gly Leu Glu Trp Ile
        35                  40                  45

Gly Tyr Ile Asn Pro Ser Arg Gly Tyr Thr Asn Tyr Asn Gln Lys Val
50                  55                  60

Lys Asp Arg Phe Thr Ile Ser Thr Asp Lys Ser Lys Ser Thr Ala Phe
65                  70                  75                  80

Leu Gln Met Asp Ser Leu Arg Pro Glu Asp Thr Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser
            115
```

(2) INFORMATION FOR SEQ ID NO: 20:

(i) SEQUENCE CHARACTERISTICS:
        (A) LENGTH: 119 amino acids
        (B) TYPE: amino acid
        (D) TOPOLOGY: linear (ii) MOLECULE TYPE: peptide (xi) SEQUENCE DESCRIPTION: SEQ ID NO: 20:

```
Gln Val Gln Leu Val Glu Ser Gly Gly Gly Val Val Gln Pro Gly Arg
1               5                   10                  15
```

Ser Leu Arg Leu Ser Cys Ser Ala Ser Gly Tyr Thr Phe Thr Arg Tyr
            20                  25                  30

Thr Met His Trp Val Arg Gln Ala Pro Cys Lys Gly Leu Glu Trp Ile
        35                  40                  45

Gly Tyr Ile Asn Pro Ser Arg Gly Tyr Thr Asn Tyr Asn Gln Lys Val
    50                  55                  60

Lys Asp Arg Phe Thr Ile Ser Thr Asp Lys Ser Lys Ser Thr Ala Phe
65                  70                  75                  80

Leu Gln Met Asp Ser Leu Arg Pro Glu Asp Thr Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser
        115

(2) INFORMATION FOR SEQ ID NO: 21:

(i) SEQUENCE CHARACTERISTICS:
        (A) LENGTH: 119 amino acids
        (B) TYPE: amino acid
        (D) TOPOLOGY: linear (ii) MOLECULE TYPE: peptide (xi) SEQUENCE DESCRIPTION: SEQ ID NO: 21:

Gln Val Gln Leu Val Glu Ser Gly Gly Gly Val Val Gln Pro Gly Arg
1               5                   10                  15

Ser Leu Arg Leu Ser Cys Ser Ser Gly Tyr Thr Phe Thr Arg Tyr
            20                  25                  30

Thr Met His Trp Val Arg Gln Ala Pro Cys Lys Gly Leu Glu Trp Ile
        35                  40                  45

Gly Tyr Ile Asn Pro Ser Arg Gly Tyr Thr Asn Tyr Asn Gln Lys Val
    50                  55                  60

Lys Asp Arg Phe Thr Ile Ser Thr Asp Lys Ser Lys Ser Thr Ala Phe
65                  70                  75                  80

Leu Gln Met Asp Ser Leu Arg Pro Glu Asp Thr Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser
        115

(2) INFORMATION FOR SEQ ID NO: 22:

(i) SEQUENCE CHARACTERISTICS:
        (A) LENGTH: 119 amino acids
        (B) TYPE: amino acid
        (D) TOPOLOGY: linear (ii) MOLECULE TYPE: peptide (xi) SEQUENCE DESCRIPTION: SEQ ID NO: 22:

Gln Val Gln Leu Val Gln Ser Gly Gly Gly Val Val Gln Pro Gly Arg
1               5                   10                  15

Ser Leu Arg Leu Ser Cys Ser Ala Ser Gly Tyr Thr Phe Thr Arg Tyr
            20                  25                  30

Thr Met His Trp Val Arg Gln Ala Pro Cys Lys Gly Leu Glu Trp Ile
        35                  40                  45

```
Gly Tyr Ile Asn Pro Ser Arg Gly Tyr Thr Asn Tyr Asn Gln Lys Val
    50                  55                  60

Lys Asp Arg Phe Thr Ile Ser Thr Asp Lys Ser Lys Ser Thr Ala Phe
65                  70                  75                  80

Leu Gln Met Asp Ser Leu Arg Pro Glu Asp Thr Gly Val Tyr Phe Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser
        115

(2) INFORMATION FOR SEQ ID NO: 23:

(i) SEQUENCE CHARACTERISTICS:
        (A) LENGTH: 119  amino acids
        (B) TYPE: amino acid
        (D) TOPOLOGY: linear (ii) MOLECULE TYPE: peptide (xi) SEQUENCE DESCRIPTION: SEQ ID NO: 23:

Gln Val Gln Leu Val Glu Ser Gly Gly Gly Val Val Gln Pro Gly Arg
1               5                   10                  15

Ser Leu Arg Leu Ser Cys Ser Ala Ser Gly Tyr Thr Phe Thr Arg Tyr
                20                  25                  30

Thr Met His Trp Val Arg Gln Ala Pro Cys Lys Gly Leu Glu Trp Ile
            35                  40                  45

Gly Tyr Ile Asn Pro Ser Arg Gly Tyr Thr Asn Tyr Asn Gln Lys Val
    50                  55                  60

Lys Asp Arg Phe Thr Ile Ser Thr Asp Lys Ser Lys Ser Thr Ala Phe
65                  70                  75                  80

Leu Gln Met Asp Ser Leu Arg Pro Glu Asp Thr Gly Val Tyr Phe Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser
        115

(2) INFORMATION FOR SEQ ID NO: 24:

(i) SEQUENCE CHARACTERISTICS:
        (A) LENGTH: 119 amino acids
        (B) TYPE: amino acid
        (D) TOPOLOGY: linear (ii) MOLECULE TYPE: peptide (xi) SEQUENCE DESCRIPTION: SEQ ID NO: 24:

Gln Val Gln Leu Val Gln Ser Gly Gly Gly Val Val Gln Pro Gly Arg
1               5                   10                  15

Ser Leu Arg Leu Ser Cys Ser Ala Ser Gly Tyr Thr Phe Thr Arg Tyr
                20                  25                  30

Thr Met His Trp Val Arg Gln Ala Pro Cys Lys Gly Leu Glu Trp Ile
            35                  40                  45

Gly Tyr Ile Asn Pro Ser Arg Gly Tyr Thr Asn Tyr Asn Gln Lys Val
    50                  55                  60

Lys Asp Arg Phe Thr Ile Ser Thr Asp Lys Ser Lys Ser Thr Ala Phe
65                  70                  75                  80

Leu Gln Met Asp Ser Leu Arg Pro Glu Asp Thr Gly Val Tyr Phe Cys
```

```
                    85                  90                  95
Ala Arg Tyr Tyr Asp Asp His Tyr Cys Leu Asp Tyr Trp Gly Gln Gly
                100                 105                 110

Thr Thr Leu Thr Val Ser Ser
        115
```

(2) INFORMATION FOR SEQ ID NO: 25:

(i) SEQUENCE CHARACTERISTICS:
        (A) LENGTH: 107 amino acids
        (B) TYPE: amino acid
        (D) TOPOLOGY: linear (ii) MOLECULE TYPE: peptide (xi) SEQUENCE DESCRIPTION: SEQ ID NO: 25:

```
Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Val Ser Tyr Met
                20                  25                  30

Asn Trp Tyr Gly Gln Thr Pro Gly Lys Ala Pro Lys Leu Leu Ile Tyr
            35                  40                  45

Asp Thr Ser Lys Leu Ala Ser Gly Val Pro Ser Arg Phe Ser Gly Ser
        50                  55                  60

Gly Ser Gly Thr Asp Tyr Thr Phe Thr Ile Ser Ser Leu Gln Pro Glu
65                  70                  75                  80

Asp Ile Ala Thr Tyr Tyr Cys Gln Gln Trp Ser Ser Asn Pro Phe Thr
                85                  90                  95

Phe Gly Gln Gly Thr Lys Leu Gln Ile Thr Arg
                100                 105
```

(2) INFORMATION FOR SEQ ID NO: 26:

(i) SEQUENCE CHARACTERISTICS:
        (A) LENGTH: 107 amino acids
        (B) TYPE: amino acid
        (D) TOPOLOGY: linear (ii) MOLECULE TYPE: peptide (xi) SEQUENCE DESCRIPTION: SEQ ID NO: 26:

```
Gln Ile Val Met Thr Gln Ser Pro Ser Ser Leu Ser Ala Ser Val Gly
1               5                   10                  15

Asp Arg Val Thr Ile Thr Cys Ser Ala Ser Ser Val Ser Tyr Met
                20                  25                  30

Asn Trp Tyr Gln Gln Thr Pro Gly Lys Ala Pro Lys Arg Trp Ile Tyr
            35                  40                  45

Asp Thr Ser Lys Leu Ala Ser Gly Val Pro Ser Arg Phe Ser Gly Ser
        50                  55                  60

Gly Ser Gly Thr Asp Tyr Thr Phe Thr Ile Ser Ser Leu Gln Pro Glu
65                  70                  75                  80

Asp Ile Ala Thr Tyr Tyr Cys Gln Gln Trp Ser Ser Asn Pro Phe Thr
                85                  90                  95

Phe Gly Gln Gly Thr Lys Leu Gln Ile Thr Arg
                100                 105
```

(2) INFORMATION FOR SEQ ID NO: 27:

(i) SEQUENCE CHARACTERISTICS:
        (A) LENGTH: 107 amino acids (B) TYPE: amino acid
(D) TOPOLOGY: linear (ii) MOLECULE TYPE: peptide (xi) SEQUENCE DESCRIPTION: SEQ ID NO: 27:

```
Gln Ile Val Met Thr Gln Ser Pro Ser Ser Leu Ser Ala Ser Val Gly
 1               5                  10                  15

Asp Arg Val Thr Ile Thr Cys Ser Ala Ser Ser Val Ser Tyr Met
             20                  25                  30

Asn Trp Tyr Gln Gln Thr Pro Gly Lys Ala Pro Lys Arg Trp Ile Tyr
             35                  40                  45

Asp Thr Ser Lys Leu Ala Ser Gly Val Pro Ser Arg Phe Ser Gly Ser
         50                  55                  60

Gly Ser Gly Thr Asp Tyr Thr Phe Thr Ile Ser Ser Leu Gln Pro Glu
 65                  70                  75                  80

Asp Ile Ala Thr Tyr Tyr Cys Gln Gln Trp Ser Ser Asn Pro Phe Thr
                 85                  90                  95

Phe Gly Gln Gly Thr Lys Leu Gln Ile Thr Arg
                100                 105
```

(2) INFORMATION FOR SEQ ID NO: 28:

(i) SEQUENCE CHARACTERISTICS:
  (A) LENGTH: 107 amino acids
  (B) TYPE: amino acid
  (D) TOPOLOGY: linear (ii) MOLECULE TYPE: peptide (xi) SEQUENCE DESCRIPTION: SEQ ID NO: 28:

```
Asp Ile Gln Met Thr Gln Ser Pro Ser Ser Leu Ser Ala Ser Val Gly
 1               5                  10                  15

Asp Arg Val Thr Ile Thr Cys Ser Ala Ser Ser Val Ser Tyr Met
             20                  25                  30

Asn Trp Tyr Gln Gln Thr Pro Gly Lys Ala Pro Lys Arg Trp Ile Tyr
             35                  40                  45

Asp Thr Ser Lys Leu Ala Ser Gly Val Pro Ser Arg Phe Ser Gly Ser
         50                  55                  60

Gly Ser Gly Thr Asp Tyr Thr Phe Thr Ile Ser Ser Leu Gln Pro Glu
 65                  70                  75                  80

Asp Ile Ala Thr Tyr Tyr Cys Gln Gln Trp Ser Ser Asn Pro Phe Thr
                 85                  90                  95

Phe Gly Gln Gly Thr Lys Leu Gln Ile Thr Arg
                100                 105
```

(2) INFORMATION FOR SEQ ID NO: 29

(i) SEQUENCE CHARACTERISTICS:
  (A) LENGTH: 107 amino acids
  (B) TYPE: amino acid
  (D) TOPOLOGY: linear (ii) MOLECULE TYPE: peptide (xi) SEQUENCE DESCRIPTION: SEQ ID NO: 29

```
                    Gln Ile Val Leu Thr Gln Ser Pro Ala Ile
                     1               5                  10

Met Ser Ala Ser Pro Gly Glu Lys Val Thr Met Thr Cys Ser Ala Ser
             15                  20                  25
```

```
                    -continued

Ser Ser Val Ser Tyr Met Asn Trp Tyr Gln Gln Lys Ser Gly Thr Ser
            30              35              40

Pro Lys Arg Trp Ile Tyr Asp Thr Ser Lys Leu Ala Ser Gly Val Pro
        45              50              55

Ala His Phe Arg Gly Ser Gly Ser Gly Thr Ser Tyr Ser Leu Thr Ile
        60              65              70

Ser Gly Met Glu Ala Glu Asp Ala Ala Thr Tyr Tyr Cys Gln Gln Trp
75              80              85              90

Ser Ser Asn Pro Phe Thr Phe Gly Ser Gly Thr Lys Leu Glu Ile Asn
                95              100             105

Arg (2) INFORMATION FOR SEQ ID NO: 30

(i) SEQUENCE CHARACTERISTICS:
        (A) LENGTH: 119  amino  acids
        (B) TYPE: amino acid
        (D) TOPOLOGY: linear (ii) MOLECULE TYPE: peptide (xi) SEQUENCE DESCRIPTION: SEQ ID NO: 30

Gln Val Gln Leu Gln Gln Ser Gly Ala Glu Leu Ala Arg
            1               5               10

Pro Gly Ala Ser Val Lys Met Ser Cys Lys Ala Ser Gly Tyr Thr Phe
    15              20              25

Thr Arg Tyr Thr Met His Trp Val Lys Gln Arg Pro Gly Gln Gly Leu
30              35              40              45

Glu Trp Ile Gly Tyr Ile Asn Pro Ser Arg Gly Tyr Thr Asn Tyr Asn
            50              55              60

Gln Lys Phe Lys Asp Lys Ala Thr Leu Thr Thr Asp Lys Ser Ser Ser
            65              70              75

Thr Ala Tyr Met Gln Leu Ser Ser Leu Thr Ser Glu Asp Ser Ala Val
            80              85              90

Tyr Tyr Cys Ala Arg Tyr Tyr Asp Asp His Tyr Cys Leu Asp Tyr Trp
            95              100             105

Gly Gln Gly Thr Thr Leu Thr Val Ser Ser
110             115
```

HUMANIZED ANTIBODIES

CROSS-REFERENCE TO RELATED APPLICATIONS

The present application is a Continuation of application Ser. No. 08/846,658, Filed on May 1, 1997, which is a Continuation of application Ser. No. 08/303,569, Filed on Sep. 7, 1994, now U.S. Pat. No. 5,859,205, Issued on Jan. 12, 1999, which is a File Wrapper Continuation of application Ser. No. 07/743,329, Filed on Sep. 17, 1991, Abandoned, which is a 371 National Phase Filing of PCT/GB90/02017, International Filing Date of Dec. 21, 1990, which claims priority to GB 8928874.0, Filed on Dec. 21, 1989, all applications incorporated by reference herein in their entireties.

FIELD OF THE INVENTION

The present invention relates to humanised antibody molecules, to processes for their production using recombinant DNA technology, and to their therapeutic uses.

The term "humanised antibody molecule" is used to describe a molecule having an antigen binding site derived from an immunoglobulin from a non-human species, and remaining immunoglobulin-derived parts of the molecule being derived from a human immunoglobulin. The antigen binding site typically comprises complementarity determining regions (CDRs) which determine the binding specificity of the antibody molecule and which are carried on appropriate framework regions in the variable domains. There are 3 CDRs (CDR1, CDR2 and CDR3) in each of the heavy and light chain variable domains.

In the description, reference is made to a number of publications by number. The publications are listed in numerical order at the end of the description.

BACKGROUND OF THE INVENTION

Natural immunoglobulins have been known for many years, as have the various fragments thereof, such as the Fab, (Fab')$_2$ and Fc fragments, which can be derived by enzymatic cleavage. Natural immunoglobulins comprise a generally Y-shaped molecule having an antigen-binding site towards the end of each upper arm. The remainder of the structure, and particularly the stem of the Y, mediates the effector functions associated with immunoglobulins.

Natural immunoglobulins have been used in assay, diagnosis and, to a more limited extent, therapy. However, such uses, especially in therapy, were hindered until recently by the polyclonal nature of natural immunoglobulins. A significant step towards the realisation of the potential of immunoglobulins as therapeutic agents was the discovery of procedures for the production of monoclonal antibodies (MAbs) of defined specificity (1).

However, most MAbs are produced by hybridomas which are fusions of rodent spleen cells with rodent myeloma cells. They are therefore essentially rodent proteins. There are very few reports of the production of human MAbs.

Since most available MAbs are of rodent origin, they are naturally antigenic in humans and thus can give rise to an undesirable immune response termed the HAMA (Human Anti-Mouse Antibody) response. Therefore, the use of rodent MAbs as therapeutic agents in humans is inherently limited by the fact that the human subject will mount an immunological response to the MAb and will either remove it entirely or at least reduce its effectiveness. In practice, MAbs of rodent origin may not be used in patients for more than one or a few treatments an a HAMA response soon develops rendering the MAb ineffective as well as giving rise to undesirable reactions. For instance, OKT3 a mouse IgG2a/k MAb which recognises an antigen in the T-cell receptor-CD3 complex has been approved for use in many countries throughout the world as an immunosuppressant in the treatment of acute allograft rejection [Chatenoud et al (2) and Jeffers et al (3)]. However, in view of the rodent nature of this and other such MAbs, a significant HAMA response which may include a major anti-idiotype component, may build up on use. Clearly, it would be highly desirable to diminish or abolish this undesirable HAMA response and thus enlarge the areas of use of these very useful antibodies.

Proposals have therefore been made to render non-human MAbs less antigenic in humans. Such techniques can be generically termed "humanisation" techniques. These techniques typically involve the use of recombinant DNA technology to manipulate DNA sequences encoding the polypeptide chains of the antibody molecule.

Early methods for humanising MAbs involved production of chimeric antibodies in which an antigen binding site comprising the complete variable domains of one antibody is linked to constant domains derived from another antibody. Methods for carrying out such chimerisation procedures are described in EP0120694 (Celltech Limited), EP0125023 (Genentech Inc. and City of Hope), EP-A-0 171496 (Res. Dev. Corp. Japan), EP-A-0 173 494 (Stanford University), and WO 86/01533 (Celltech Limited). This latter Celltech application (WO 86/01533) discloses a process for preparing an antibody molecule having the variable domains from a mouse MAb and the constant domains from a human immunoglobulin. Such humanised chimeric antibodies, however, still contain a significant proportion of non-human amino acid sequence, i.e. the complete non-human variable domains, and thus may still elicit some HAMA response, particularly if administered over a prolonged period [Begent et al (ref. 4)].

In an alternative approach, described in EP-A-0239400 (Winter), the complementarity determining regions (CDRs) of a mouse MAb have been grafted onto the framework regions of the variable domains of a human immunoglobulin by site directed mutagenesis using long oligonucleotides. The present invention relates to humanised antibody molecules prepared according to this alternative approach, i.e. CDR-grafted humanised antibody molecules. Such CDR-grafted humanised antibodies are much less likely to give rise to a HAMA response than humanized chimeric antibodies in view of the much lower proportion of non-human amino acid sequence which they contain.

The earliest work on humanising MAbs by CDR-grafting was carried out on MAbs recognizing synthetic antigens, such as the NP or NIP antigens. However, examples in which a mouse MAb recognising lysozyme and a rat MAb recognising an antigen on human T-cells were humanised by CDR-grafting have been described by Verhoeyou et al (5) and Riechmann et al (6) respectively. The preparation of CDR-grafted antibody to the antigen on human T cells is also described in WO 89/07452 (Medical Research Council).

In Riechmann et al/Medical Research Council it was found that transfer of the CDR regions alone [as defined by Kabat refs. (7) and (8)] was not sufficient to provide satisfactory antigen binding activity in the CDR-grafted product. Riechmann et al found that it was necessary to convert a serine residue at position 27 of the human sequence to the corresponding rat phenylalanine residue to obtain a CDR-grafted product having improved antigen binding activity. This residue at position 27 of the heavy chain is within the structural loop adjacent to CDR1. A further construct which additionally contained a human serine to rat tyrosine change at position 30 of the heavy chain did not have a significantly altered binding activity over the humanised antibody with the serine to phenylalanine change at position 27 alone. These results indicate that changes to residues of the human sequence outside the CDR regions, in particular in the structural loop adjacent to CDR1, may be necessary to obtain effective antigen binding activity for CDR-grafted antibodies which recognise more complex antigens. Even so the binding affinity of the best CDR-grafted antibodies obtained was still significantly less than the original MAb.

Very recently Queen et al (9) have described the preparation of a humanised antibody that binds to the interleukin 2 receptor, by combining the CDRs of a murine MAb (anti-Tac) with human immunoglobulin framework and constant regions. The human framework regions were chosen to maximise homology with the anti-Tac MAb sequence. In addition computer modelling was used to identify framework amino acid residues which were likely to interact with the CDRs or antigen, and mouse amino acids were used at these positions in the humanised antibody.

In WO 90/07861 Queen at al propose four criteria for designing humanised immunoglobulins. The first criterion is to use as the human acceptor the framework from a particular human immunoglobulin that is unusually homologous to the non-human donor immunoglobulin to be humanised, or to use a consensus framework from many human antibodies. The second criterion is to use the donor amino acid rather than the acceptor if the human acceptor residue is unusual and the donor residue is typical for human sequences at a specific residue of the framework. The third criterion is to use the donor framework amino acid residue rather than the acceptor at positions immediately adjacent to the CDRs. The fourth criterion is to use the donor amino acid residue at framework positions at which the amino acid is predicted to have a side chain atom within about 3 Å of the CDRs in a three-dimensional immunoglobulin model and to be capable of interacting with the antigen or with the CDRs of the humanised immunoglobulin. It is proposed that criteria two, three or four may be applied in addition or alternatively to criterion one, and may be applied singly or in any combination.

WO 90/07861 describes in detail the preparation of a single CDR-grafted humanised antibody, a humanised antibody having specificity for the p55 Tac protein of the IL-2 receptor. The combination for all four criteria, as above, were employed in designing this humanised antibody, the variable region frameworks of the human antibody Eu (7) being used as acceptor. In the resultant humanised antibody the donor CDRs were as defined by Kabat et al (7 and 8) and in addition the mouse donor residues were used in place of the human acceptor residues, at positions 27, 30, 41, 66, 67, 89, 91, 94, 103, 104, 105 and 107 in the heavy chain and at positions 48, 60 and 63 in the light chain, of the variable region frameworks. The humanised anti-Tac antibody obtained is reported to have an affinity for p55 of $3 \times 10^9$ M$^{-1}$, about one-third of that of the murine MAb.

We have further investigated the preparation of CDR-grafted humanised antibody molecules and have identified a hierarchy of positions within the framework of the variable regions (i.e. outside both the Kabat CDRs and structural loops of the variable regions) at which the amino acid identities of the residues are important for obtaining CDR-grafted products with satisfactory binding affinity. This has enabled us to establish a protocol for obtaining satisfactory CDR-grafted products which may be applied very widely irrespective of the level of homology between the donor immunoglobulin and acceptor framework. The set of residues which we have identified as being of critical importance does not coincide with the residues identified by Queen et al (9).

SUMMARY OF THE INVENTION

Accordingly, in a first aspect the invention provides a CDR-grafted antibody heavy chain having a variable region domain comprising acceptor framework and donor antigen binding regions wherein the framework comprises donor residues at at least one of positions 6, 23 and/or 24, 48 and/or 49, 71 and/or 73, 75 and/or 76 and/or 78 and 88 and/or 91.

In preferred embodiments, the heavy chain framework comprises donor residues at positions 23, 24, 49, 71, 73 and 78 or at positions 23, 24 and 49. The residues at positions 71, 73 and 78 of the heavy chain framework are preferably either all acceptor or all donor residues.

In particularly preferred embodiments the heavy chain framework additionally comprises donor residues at one, some or all of positions 6, 37, 48 and 94. Also it is particularly preferred that residues at positions of the heavy chain framework which are commonly conserved across species, i.e. positions 2, 4, 25, 36, 39, 47, 93, 103, 104, 106 and 107, if not conserved between donor and acceptor, additionally comprise donor residues. Most preferably the heavy chain framework additionally comprises donor residues at positions 2, 4, 6, 25, 36, 37, 39, 47, 48, 93, 94, 103, 104, 106 and 107.

In addition the heavy chain framework optionally comprises donor residues at one, some or all of positions:
1 and 3,
72 and 76,
69 (if 48 is different between donor and acceptor),
38 and 46 (if 48 is the donor residue),
80 and 20 (if 69 is the donor residue),
67,
82 and 18 (if 67 is the donor residue),
91,
88, and
any one or more of 9, 11, 41, 87, 108, 110 and 112.

In the first and other aspects of the present invention reference is made to CDR-grafted antibody products comprising acceptor framework and donor antigen binding regions. It will be appreciated that the invention is widely applicable to the CDR-grafting of antibodies in general. Thus, the donor and acceptor antibodies may be derived from animals for the same species and even same antibody class or sub-class. More usually, however, the donor and acceptor antibodies are derived from animals of different species. Typically the donor antibody is a non-human antibody, such as a rodent MAb, and the acceptor antibody is a human antibody.

In the first and other aspects of the present invention, the donor antigen binding region typically comprises at least one CDR from the donor antibody. Usually the donor antigen binding region comprises at least two and preferably all three CDRs of each of the heavy chain and/or light chain variable regions. The CDRs may comprise the Kabat CDRs, the structural loop CDRs or a composite of the Kabat and structural loop CDRs and any combination of any of these. Preferably, the antigen binding regions of the CDR-grafted heavy chain variable domain comprise CDRs corresponding to the Kabat CDRs at CDR2 (residues 50–65) and CDR3

(residues 95–100) and a composite of the Kabat and structural loop CDRs at CDR1 (residues 26–35).

The residue designations given above and elsewhere in the present application are numbered according to the Kabat numbering [refs. (7) and (8)]. Thus the residue designations do not always correspond directly with the linear numbering of the amino acid residues. The actual linear amino acid sequence may contain fewer or additional amino acids than in the strict Kabat numbering corresponding to a shortening of, or insertion into, a structural component, whether framework or CDR, of the basic variable domain structure. For example, the heavy chain variable region of the anti-Tac antibody described by Queen et al (9) contains a single amino acid insert (residue 52a) after residue 52 of CDR2 and a three amino acid insert (residues 82a, 82b and 82c) after framework residue 82, in the Kabat numbering. The correct Kabat numbering of residues may be determined for a given antibody by alignment at regions of homology of the sequence of the antibody with a "standard" Kabat numbered sequence.

The invention also provides in a second aspect a CDR-grafted antibody light chain having a variable region domain comprising acceptor framework and donor antigen binding regions wherein the framework comprises donor residues at at least one of positions 1 and/or 3 and 46 and/or 47. Preferably the CDR grafted light chain of the second aspect comprises donor residues at positions 46 and/or 47.

The invention also provides in a third aspect a CDR-grafted antibody light chain having a variable region domain comprising acceptor framework and donor antigen binding regions wherein the framework comprises donor residues at at least one of positions 46, 48, 58 and 71.

In a preferred embodiment of the third aspect, the framework comprises donor residues at all of positions 46, 48, 58 and 71.

In particularly preferred embodiments of the second and third aspects, the framework additionally comprises donor residues at positions 36, 44, 47, 85 and 87. Similarly positions of the light chain framework which are commonly conserved across species, i.e. positions 2, 4, 6, 35, 49, 62, 64–69, 98, 99, 101 and 102, if not conserved between donor and acceptor, additionally comprise donor residues. Most preferably the light chain framework additionally comprises donor residues at positions 2, 4, 6, 35, 36, 38, 44, 47, 49, 62, 64–69, 85, 87, 98, 99, 101 and 102.

In addition the framework of the second or third aspects optionally comprises donor residues at one, some or all of positions:
1 and 3,
63,
60 (if 60 and 54 are able to form at potential saltbridge),
70 (if 70 and 24 are able to form a potential saltbridge),
73 and 21 (if 47 is different between donor and acceptor),
37 and 45 (if 47 is different between donor and acceptor), and
any one or more of 10, 12, 40, 80, 103 and 105.

Preferably, the antigen binding regions of the CDR-grafted light chain variable domain comprise CDRs corresponding to the Kabat CDRs at CDR1 (residue 24–34), CDR2 (residues 50–56) and CDR3 (residues 89–97).

The invention further provides in a fourth aspect a CDR-grafted antibody molecule comprising at least one CDR-grafted heavy chain and at least one CDR-grafted light chain according to the first and second or first and third aspects of the invention.

The humanised antibody molecules and chains of the present invention may comprise: a complete antibody molecule, having full length heavy and light chains; a fragment thereof, such as a Fab, (Fab')$_2$ or FV fragment; a light chain or heavy chain monomer or dimer; or a single chain antibody, e.g. a single chain FV in which heavy and light chain variable regions are joined by a peptide linker; or any other CDR-grafted molecule with the same specificity as the original donor antibody. Similarly the CDR-grafted heavy and light chain variable region may be combined with other antibody domains as appropriate.

Also, the heavy or light chains or humanised antibody molecules of the present invention may have attached to them an effector or reporter molecule. For instance, it may have a macrocycle, for chelating a heavy metal atom, or a toxin, such as ricin, attached to it by a covalent bridging structure. Alternatively, the procedures of recombinant DNA technology may be used to produce an immunoglobulin molecule in which the Fc fragment or CH3 domain of a complete immunoglobulin molecule has been replaced by, or has attached thereto by peptide linkage, a functional non-immunoglobulin protein, such as an enzyme or toxin molecule.

Any appropriate acceptor variable region framework sequences may be used having regard to class/type of the donor antibody from which the antigen binding regions are derived. Preferably, the type of acceptor framework used is of the same/similar class/type as the donor antibody. Conveniently, the framework may be chosen to maximise/optimise homology with the donor antibody sequence particularly at positions close or adjacent to the CDRs. However, a high level of homology between donor and acceptor sequences is not important for application of the present invention. The present invention identifies a hierarchy of framework residue positions at which donor residues may be important or desirable for obtaining a CDR-grafted antibody product having satisfactory binding properties. The CDR-grafted products usually have binding affinities of at least $10^5$ M$^{-1}$, preferably at least about $10^8$ M$^{-1}$, or especially in the range $10^8$–$10^{12}$ M$^{-1}$. In principle, the present invention is applicable to any combination of donor and acceptor antibodies irrespective of the level of homology between their sequences. A protocol for applying the invention to any particular donor-acceptor antibody pair is given hereinafter. Examples of human frameworks which may be used are KOL, NEWM, REI, EU, LAY and POM (refs. 4 and 5) and the like; for instance KOL and NEWM for the heavy chain and REI for the light chain and EU, LAY and POM for both the heavy chain and the light chain.

Also the constant region domains of the products of the invention may be selected having regard to the proposed function of the antibody in particular the effector functions which may be required. For example, the constant region domains may be human IgA, IgE, IgG or IgM domains. In particular, IgG human constant region domains may be used, especially of the IgG1 and IgG3 isotypes, when the humanised antibody molecule is intended for therapeutic uses, and antibody effector functions are required. Alternatively, IgG2 and IqG4 isotypes may be used when the humanised antibody molecule is intended for therapeutic purposes and antibody effector functions are not required, e.g. for simple blocking of lymphokine activity.

However, the remainder of the antibody molecules need not comprise only protein sequences from immunoglobulins. For instance, a gone may be constructed in which a DNA sequence encoding part of a human immunoglobulin chain is fused to a DNA sequence encoding the amino acid sequence of a functional polypeptide such as an effector or reporter molecule.

Preferably the CDR-grafted antibody heavy and light chain and antibody molecule products are produced by recombinant DNA technology.

Thus in further aspects the invention also includes DNA sequences coding for the CDR-grafted heavy and light chains, cloning and expression vectors containing the DNA sequences, host cells transformed with the DNA sequences and processes for producing the CDR-grafted chains and antibody molecules comprising expressing the DNA sequences in the transformed host cells.

The general methods by which the vectors may be constructed, transfection methods and culture methods are well known per se and form no part of the invention. Such methods are shown, for instance, in references 10 and 11.

The DNA sequences which encode the donor amino acid sequence may be obtained by methods well known in the art. For example the donor coding sequences may be obtained by genomic cloning, or cDNA cloning from suitable hybridoma cell lines. Positive clones may be screened using appropriate probes for the heavy and light chain genes in question. Also PCR cloning may be used.

DNA coding for acceptor, e.g. human acceptor, sequences may be obtained in any appropriate way. For example DNA sequences coding for preferred human acceptor frameworks such as KOL, REI, EU and NEWM, are widely available to workers in the art.

The standard techniques of molecular biology may be used to prepare DNA sequences coding for the CDR-grafted products. Desired DNA sequences may be synthesised completely or in part using oligonucleotide synthesis techniques. Site-directed mutagenesis and polymerase chain reaction (PCR) techniques may be used as appropriate. For example oligonucleotide directed synthesis as described by Jones et al (ref. 20) may be used. Also oligonucleotide directed mutagenesis of a pre-exising variable region as, for example, described by Verhoeyen et al (ref. 5) or Riechmann et al (ref. 6) may be used. Also enzymatic filling in of gapped ligonucleatides using $T_4$ DNA polymerase as, for example, described by Queen et al (ref. 9) may be used.

Any suitable host call/vector system may be used for expression of the DNA sequences coding for the CDR-grafted heavy and light chains. Bacterial e.g. *E. coli*, and other microbial systems may be used, in particular for expression of antibody fragments such as FAb and (Fab')$_2$ fragments, and especially FV fragments and single chain antibody fragments e.g. single chain FVs. Eucaryotic e.g. mammalian host cell expression systems may be used for production of larger CDR-grafted antibody products, including complete antibody molecules. Suitable mammalian host cells include CHO cells and myeloma or hybridoma cell lines.

Thus, in a further aspect the present invention provides a process for producing a CDR-grafted antibody product comprising:
(a) producing in an expression vector an operon having a DNA sequence which encodes an antibody heavy chain according to the first aspect of the invention;

and/or (b) producing in an expression vector an operon having a DNA sequence which encodes a complementary antibody light chain according to the second or third aspect of the invention;
(c) transfecting a host cell with the or each vector; and
(d) culturing the transfected cell line to produce the CDR-grafted antibody product.

The CDR-grafted product may comprise only heavy or light chain derived polypeptide, in which case only a heavy chain or light chain polypeptide coding sequence is used to transfect the host cells.

For production of products comprising both heavy and light chains, the cell line may be transfected with two vectors, the first vector may contain an operon encoding a light chain-derived polypeptide and the second vector containing an operon encoding a heavy chain-derived polypeptide. Preferably, the vectors are identical, except in so far as the coding sequences and selectable markers are concerned, so as to ensure as far as possible that each polypeptide chain is equally expressed. Alternatively, a single vector may be used, the vector including the sequences encoding both light chain- and heavy chain-derived polypeptides.

The DNA in the coding sequences for the light and heavy chains may comprise cDNA or genomic DNA or both. However, it is preferred that the DNA sequence encoding the heavy or light chain comprises at least partially, genomic DNA, preferably a fusion of cDNA and genomic DNA.

The present invention is applicable to antibodies of any appropriate specificity. Advantageously, however, the invention may be applied to the humanisation of non-human antibodies which are used for in vivo therapy or diagnosis. Thus the antibodies may be site-specific antibodies such as tumour-specific or cell surface-specific antibodies, suitable for use in in vivo therapy or diagnosis, e.g. tumour imaging. Examples of cell surface-specific antibodies are anti-T cell antibodies, such as anti-CD3, and CD4 and adhesion molecules, such as CR3, ICAM and ELAM. The antibodies may have specificity for interleukins (including lymphokines, growth factors and stimulating factors), hormones and other biologically active compounds, and receptors for any of these. For example, the antibodies may have specificity for any of the following: Inteferons $\alpha$, $\beta$, $\gamma$ or $\delta$, IL1, IL2, IL3, or IL4, etc., TNF, GCSF, GMCSF, EPO, hGH, or insulin, etc.

The present invention also includes therapeutic and diagnostic compositions comprising the CDR-grafted products of the invention and uses of such compositions in therapy and diagnosis.

Accordingly in a further aspect the invention provides a therapeutic or diagnostic composition comprising a CDR-grafted antibody heavy or light chain or molecule according to previous aspects of the invention in combination with a pharmaceutically acceptable carrier, diluent or excipient.

Accordingly also the invention provides a method of therapy or diagnosis comprising administering an effective amount of a CDR-grafted antibody heavy or light chain or molecule according to previous aspects of the invention to a human or animal subject.

A preferred protocol for obtaining CDR-grafted antibody heavy and light chains in accordance with the present invention is set out below together with the rationale by which we have derived this protocol. This protocol and rationale are given without prejudice to the generality of the invention as hereinbefore described and defined.

Protocol

It is first of all necessary to sequence the DNA coding for the heavy and light chain variable regions of the donor antibody, to determine their amino acid sequences. It is also necessary to choose appropriate acceptor heavy and light chain variable regions, of known amino acid sequence. The CDR-grafted chain is then designed starting from the basis of the acceptor sequence. It will be appreciated that in some cases the donor and acceptor amino acid residues may be identical at a particular position and thus no change of acceptor framework residue is required.

1. As a first step donor residues are substituted for acceptor residues in the CDRs. For this purpose the CDRs are preferably defined as follows:

|  |  |  |
|---|---|---|
| Heavy chain | CDR1: | residues 26–35 |
|  | CDR2: | residues 50–65 |
|  | CDR3: | residues 95–102 |
| Light chain | CDR1: | residues 24–34 |
|  | CDR2: | residues 50–56 |
|  | CDR3: | residues 89–97 |

The positions at which donor residues are to be substituted for acceptor in the framework are then chosen as follows, first of all with respect to the heavy chain and subsequently with respect to the light chain.

2. Heavy Chain 2.1 Choose donor residues at all of positions 23, 24, 49, 71, 73 and 78 of the heavy chain or all of positions 23, 24 and 49 (71, 73 and 78 are always either all donor or all acceptor).

2.2 Check that the following have the same amino acid in donor and acceptor sequences, and if not preferably choose the donor: 2, 4, 6, 25, 36, 37, 39, 47, 48, 93, 94, 103, 104, 106 and 107.

2.3 To further optimise affinity consider choosing donor residues at one, some or any of:
  i. 1, 3
  ii. 72, 76
  iii. If 48 is different between donor and acceptor sequences, consider 69
  iv. If at 48 the donor residue is chosen, consider 38 and 46
  v. If at 69 the donor residue is chosen, consider 80 and then 20
  vi. 67
  vii. If at 67 the donor residue is chosen, consider 82 and then 18
  viii. 91
  ix. 88
  x. 9, 11, 41, 87, 108, 110, 112

3. Light Chain 3.1 Choose donor at 46, 48, 58 and 71

3.2 Check that the following have the same amino acid in donor and acceptor sequences, if not preferably choose donor:
  2, 4, 6, 35, 38, 44, 47, 49, 62, 64–69 inclusive, 85, 87, 98, 99, 101 and 102

3.3 To further optimise affinity consider choosing donor residues at one, some or any of:
  i. 1, 3
  ii. 63
  iii. 60, if 60 and 54 are able to form potential saltbridge
  iv. 70, if 70 and 24 are able to form potential saltbridge
  v. 73, and 21 if 47 is different between donor and acceptor
  vi. 37, and 45 if 47 is different between donor and acceptor
  vii. 10, 12, 40, 80, 103, 105

Rationale

In order to transfer the binding site of an antibody into a different acceptor framework, a number of factors need to be considered.

1. The extent of the CDRs

The CDRs (Complementary Determining Regions) were defined by Wu and Kabat (refs. 4 and 5) on the basis of an analysis of the variability of different regions of antibody variable regions. Three regions per domain were recognised. In the light chain the sequences are 24–34, 50–56, 89–97 (numbering according to Kabat (ref. 4), Eu Index) inclusive and in the heavy chain the sequences are 31–35, 50–65 and 95–102 inclusive.

When antibody structures became available it became apparent that these CDR regions corresponded in the main to loop regions which extended from the β barrel framework of the light and heavy variable domains. For H1 there was a discrepancy in that the loop was from 26 to 32 inclusive and for H2 the loop was 52 to 56 and for L2 from 50 to 53. However, with the exception of H1 the CDR regions encompassed the loop regions and extended into the β strand frameworks. In H1 reside 26 tends to be a serine and 27 a phenylalanine or tyrosine, reside 29 is a phenylalanine in most cases. Residues 28 and 30 which are surface residues exposed to solvent might be involved in antigen-binding. A prudent definition of the H1 CDR therefore would include residues 26–35 to include both the loop region and the hypervariable residues 33–35.

It is of interest to note the example of Riechmann et al (ref. 3), who used the residue 31–35 choice for CDR-H1. In order to produce efficient antigen binding, residue 27 also needed to be recruited from the donor (rat) antibody.

2. Non-CDR residues which contribute to antigen binding

By examination of available X-ray structures we have identified a number of residues which may have an effect on net antigen binding and which can be demonstrated by experiment. These residues can be sub-divided into a number of groups.

2.1 Surface residues near CDR [all numbering as in Kabat et al (ref. 7)].

2.1.1. Heavy Chain—Key residues are 23, 71 and 73. Other residues which may contribute to a lesser extent are 1, 3 and 76. Finally 25 is usually conserved but the marine residue should be used if there is a difference.

2.1.2 Light Chain—Many residues close to the CDRs, e.g. 63, 65, 67 and 69 are conserved. If conserved none of the surface residues in the light chain are likely to have a major effect. However, if the murine residue at these positions is unusual, then it would be of benefit to analyze the likely contribution more closely. Other residues which may also contribute to binding are 1 and 3, and also 60 and 70 if the residues at these positions and at 54 and 24 respectively are potentially able to form a salt bridge i.e. 60+54; 70+24.

2.2 Packing residues near the CDRs.

2.2.1. Heavy Chain—Key residues are 24, 49 and 78. Other key residues would be 36 if not a tryptophan, 94 if not an arginine, 104 and 106 if not glycines and 107 if not a threonine. Residues which may make a further contribution to stable packing of the heavy chain and hence improved affinity are 2, 4, 6, 38, 46, 67 and 69. 67 packs against the CDR residue 63 and this pair could be either both mouse or both human. Finally, residues which contribute to packing in this region but from a longer range are 18, 20, 80, 82 and 86. 82 packs against 67 and in turn 18 packs against 82. 80 packs against 69 and in turn 20 packs against 80. 86 forms an H bond network with 38 and 46. Many of the mouse-human differences appear minor e.g. Leu-Ile, but could have an minor impact on correct packing which could translate into altered positioning of the CDRs.

2.2.2. Light Chain—Key residues are 48, 58 and 71. Other key residues would be 6 if not glutamine, if not tryptophan, 62 if not phenylalanine or tryosine, 64, 66, 68, 99 and 101 if not glycines and 102 if not a threonine. Residues which make a further contribution are 2, 4, 37, 45 and 47. Finally residues 73 and 21 and 19 may make long distance packing contributions of a minor nature.

2.3. Residues at the variable domain interface between heavy and light chains—In both the light and heavy chains most of the non-CDR interface residues are conserved. If a conserved residue is replaced by a residue of different character, e.g. size or charge, it should be considered for retention as the murine residue.

2.3.1. Heavy Chain—Residues which need to be considered are 37 if the residue is not a valine but is of larger side chain volume or has a charge or polarity. Other residues are 39 if not a glutamine, 45 if not a leucine, 47 if not a tryptophan, 91 if not a phenylalanine or tyrosine, 93 if not an alanine and 103 if not a tryptophan. Residue 89 is also at the interface but is not in a position where the side chain could be of great impact.

2.3.2. Light Chain—Residues which need to be considered are 36, if not a tyrosine, 38 if not a glutamine, 44 if not a proline, 46, 49 if not a tyrosine, residue 85, residue 87 if not a tyrosine and 98 if not a phenylalanine.

2.4. Variable-Constant region interface—The elbow angle between variable and constant regions may be affected by alterations in packing of key residues in the variable region against the constant region which may affect the position of $V_L$ and $V_H$ with respect to one another. Therefore it is worth noting the residues likely to be in contact with the constant region. In the heavy chain the surface residues potentially in contact with the variable region are conserved between mouse and human antibodies therefore the variable region contact residues may influence the V-C interaction. In the light chain the amino acids found at a number of the constant region contact points vary, and the V & C regions are not in such close proximity as the heavy chain. Therefor the influences of the light chain V-C interface may be minor.

2.4.1. Heavy Chain—Contact residues are 7, 11, 41, 87, 108, 110, 112.

2.4.2. Light Chain—In the light chain potentially contacting residues are 10, 12, 40, 80, 83, 103 and 105.

The above analysis coupled with our considerable practical experimental experience in the CDR-grafting of a number of different antibodies have lead us to the protocol given above.

The present invention is now described, by way of example only, with reference to the accompanying FIGS. 1–13.

BRIEF DESCRIPTION OF THE FIGURES

FIGS. 1a and b show DNA and amino acid sequences of the OKT3 light chain (SEQ ID NO:4);

FIGS. 2a and b show DNA and amino acid sequences of the OKT3 heavy chain (SEQ ID NO:6 and 7);

FIG. 3 shows the alignment of the OKT3 light variable region amino acid sequence with that of the light variable region of the human antibody REI (SEQ ID NO:29, 8 and 9);

FIG. 4 shows the alignment of the OKT3 heavy variable region amino acid sequence with that of the heavy variable region of the human antibody KOL (SEQ ID NO:30 and 10);

FIGS. 5a–c show the heavy variable region amino acid sequences of OKT3, KOL and various corresponding CDR grafts (SEQ ID NO:30 and 11–24);

FIG. 6 shows the light variable region amino acid sequences of OKT3, REI and various corresponding CDR grafts (SEQ ID NO:29, 8, 9, and 25–28);

DETAILED DESCRIPTION OF EMBODIMENTS OF THE INVENTION

EXAMPLE 1

CDR-Grafting of OKT3

Material and Methods

1. INCOMING CELLS

Figure 7:
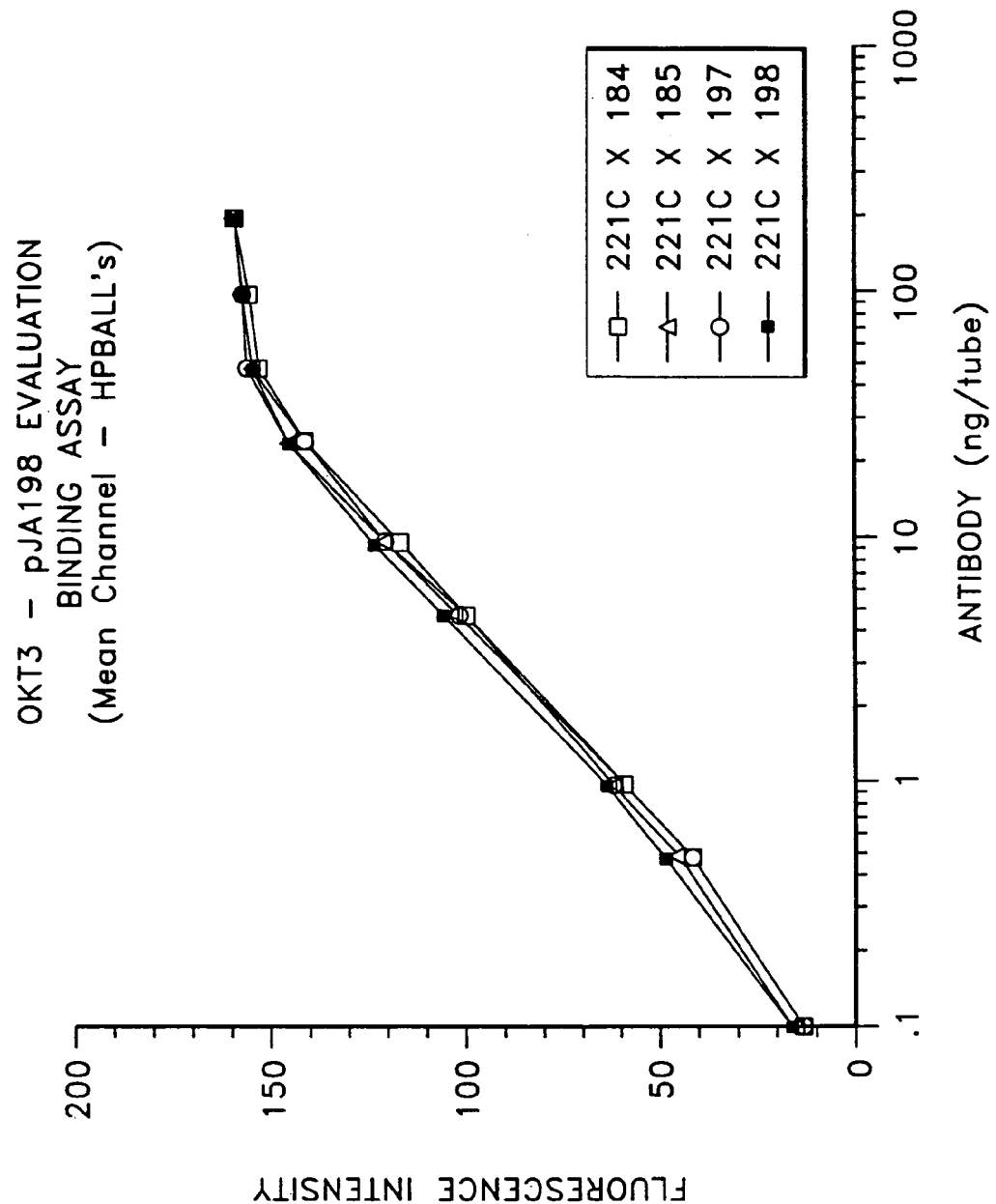
FIG. 7 shows a graph of binding assay results for various grafted OKT3 antibodies.

Hybridoma cells producing antibody OKT3 were provided by Ortho (seedlot 4882.1) and were grown up in antibiotic free Dulbecco's Modified Eagles Medium (DMEM) supplemented with glutamine and 5% foetal calf serum, and divided to provide both an overgrown supernatant for evaluation and cells for extraction of RNA. The overgrown supernatant was shown to contain 250 ug/mL murine IgG2a/kappa antibody. The supernatant was negative for murine lambda light chain and IgG1, IgG2b, IgG3, IgA and IgM heavy chain. 20 mL of supernatant was assayed to confirm that the antibody present was OKT3.

2. MOLECULAR BIOLOGY PROCEDURES

Basic molecular biology procedures were as described in Maniatis et al (ref. 9) with, in some cases, minor modifications. DNA sequencing was performed as described in Sanger et al (ref. 11) and the Amersham International Plc sequencing handbook. Site directed mutagenesis was as described in Kramer et al (ref. 12) and the Anglian Biotechnology Ltd. handbook. COS cell expression and metabolic labelling studies were as described in Whittle et al (ref. 13)

3. RESEARCH ASSAYS 3.1. ASSEMBLY ASSAYS

Assembly assays were performed on supernatants from transfected COS cells to determine the amount of intact IgG present.

3.1.1. COS CELLS TRANSFECTED WITH MOUSE OKT3 GENES

The assembly assay for intact mouse IgG in COS cell supernatants was an ELISA with the following format: 96 well microtitre plates were coated with F(ab')$_2$ goat anti-mouse IgG Fc. The plates were washed in water and samples added for 1 hour at room temperature. The plates were washed and F(ab')$_2$ goat anti-mouse IgG F(ab')$_2$ (HRPO conjugated) was then added. Substrate was added to reveal the reaction. UPC10, a mouse IgG2a myeloma, was used as a standard.

3.1.2. COS AND CHO CELL TRANSFECTED WITH CHIMERIC OR CDR-GRAFTED OKT3 GENES

The assembly assay for chimeric or CDR-grafted antibody in COS cell supernatants was an ELISA with the following format:

96 well microtitre plates were coated with F(ab')$_2$ goat anti-human IgG Fc. The plates were washed and samples added and incubated for 1 hour at room temperature. The plates were washed and monoclonal mouse anti-human kappa chain was added for 1 hour at room temperature.

The plates were washed and F(ab')$_2$ goat anti-mouse IgG Fc (HRPO conjugated) was added. Enzyme substrate was added to reveal the reaction. Chimeric B72.3 (IgG4) (ref. 13) was used as a standard. The use of a monoclonal anti-kappa chain in this assay allows grafted antibodies to be read from the chimeric standard.

3.2. ASSAY FOR ANTIGEN BINDING ACTIVITY

Material from COS cell supernatants was assayed for OKT3 antigen binding activity onto CD3 positive cells in a direct assay. The procedure was as follows:

HUT 78 cells (human T cell line, CD3 positive) were maintained in culture. Monolayers of HUT 78 cells were prepared onto 96 well ELISA plates using poly-L-lysine and glutaraldehyde. Samples were added to the monolayers for 1 hour at room temperature.

The plates were washed gently using PBS. F(ab')$_2$ goat anti-human IgG Pc (ERPO conjugated) or F(ab')$_2$ goat anti-mouse IgG Fc (ERPO conjugated) was added as appropriate for humanised or mouse samples. Substrate was added to reveal the reaction.

The negative control for the cell-based assay was chimeric B72.3. The positive control was mouse Orthomune OKT3 or chimeric OKT3, when available. This cell-based assay was difficult to perform, and an alternative assay was developed for CDR-grafted OKT3 which was more sensitive and easier to carry out.

In this system CDR-grafted OKT3 produced by COS cells was tested for its ability to bind to the CD3-positive HPB-ALL (human peripheral blood acute lymphocytic leukemia) cell line. It was also tested for its ability to block the binding of murine OKT3 to these cells. Binding was measured by the following procedure: HPB-ALL cells were harvested from tissue culture. Cells were incubated at 4° C. for 1 hour with various dilutions of test antibody, positive control antibody, or negative control antibody. The cells were washed once and incubated at 4° C. for 1 hour with an FITC-labelled goat anti-human IgG (Fc-specific, mouse absorbed). The cells were washed twice and analysed by cytofluorography. Chimeric OKT3 was used as a positive control for direct binding. Cells incubated with mock-transfected COS call supernatant, followed by the FITC-labelled goat anti-human IgG, provided the negative control. To test the ability of CDR-grafted OKT3 to block murine OKT3 binding, the HPB-ALL cells were incubated at 40° C. for 1 hour with various dilutions of test antibody or control antibody. A fixed saturating amount of FITC OKT3 was added. The samples were incubated for 1 hour at 4° C., washed twice and analysed by cytofluorography.

FITC-labelled OKT3 was used as a positive control to determine maximum binding. Unlabelled murine OKT3 served as a reference standard for blocking. Negative controls were unstained cells with or without mock-transfected cell supernatant. The ability of the CDR-grafted OKT3 light chain to bind CD3-positive cells and block the binding of murine OKT3 was initially tested in combination with the chimeric OKT3 heavy chain. The chimeric OKT3 heavy chain is composed of the murine OKT3 variable region and the human IgG4 constant region. The chimeric heavy chain gene is expressed in the same expression vector used for the CDR-grafted genes. The CDR-grafted light chain expression vector and the chimeric heavy chain expression vector were co-transfected into COS cells. The fully chimeric OKT3 antibody (chimeric light chain and chimeric heavy chain) was found to be fully capable of binding to CD3 positive calls and blocking the binding of murine OKT3 to these cells.

3.3 DETERMINATION OF RELATIVE BINDING AFFINITY

The relative binding affinities of CDR-grafted anti-CD3 monoclonal antibodies were determined by competition binding (ref. 6) using the HPB-ALL human T cell line as a source of CD3 antigen, and fluorescein-conjugated murine OKT3 (F1-OKT3) of known binding affinity as a tracer antibody. The binding affinity of F1-OKT3 tracer antibody was determined by a direct binding assay in which increasing amounts of F1-OKT3 were incubated with HPB-ALL ($5 \times 10^5$) in PBS with 5% foetal calf serum for 60 min. at 40° C. Calls were washed, and the fluorescence intensity was determined on a FACScan flow cytometer calibrated with quantitative microbead standards (Plow Cytometry Standards, Research Triangle Park, NC). Fluorescence intensity per antibody molecule (F/P ratio) was determined by using microbeads which have a predetermined number of mouse IgG antibody binding sites (Simply Cellular beads, Flow Cytometry Standards). F/P equals the fluorescence intensity of beads saturated with F1-OKT3 divided by the number of binding sites per bead. The amount of bound and free F1-OKT3 was calculated from the mean fluorescence intensity per cell, and the ratio of bound/free was plotted against the number of moles of antibody bound. A linear fit was used to determine the affinity of binding (absolute value of the slope).

For competitive binding, increasing amounts of competitor antibody were added to a sub-saturating dose of F1-OKT3 and incubated with $5 \times 10^5$ HPB-ALL in 200 ml of PBS with 5% foetal calf serum, for 60 min at 4° C. The fluorescence intensities of the cells were measured on a FACScan flow cytometer calibrated with quantitative microbead standards. The concentrations of bound and free F1-OKT3 were calculated. The affinities of competing anti-bodies were calculated from the equation $[X]-[OKT3]=(1/K_x)-(1/K_a)$, where $K_a$ is the affinity of murine OKT3, $K_x$ is the affinity of competitor X, [ ] in the concentration of competitor antibody at which bound/free binding is R/2, and R is the maximal bound/free binding.

4. cDNA LIBRARY CONSTRUCTION

4.1. mRNA PREPARATION AND cDNA SYNTHESIS

OKT3 producing calls were grown as described above and $1.2 \times 10^9$ cells harvested and mRNA extracted using the guanidinium/LiCl extraction procedure. cDNA was prepared by priming from Oligo-dT to generate full length cDNA. The cDNA was methylated and EcoR1 linkers added for cloning.

4.2. LIBRARY CONSTRUCTION

The cDNA library was ligated to pSP65 vector DNA which had been EcoR1 cut and the 5' phosphate groups removed by calf intestinal phosphatase (EcoR1/CIP). The ligation was used to transform high transformation efficiency *Escherichia coli* (*E. coli*) HB101. A cDNA library was prepared. 3600 colonies were screened for the light chain and 10000 colonies were screened for the heavy chain.

5. SCREENING

*E. coli* colonies positive for either heavy or light chain probes were identified by oligonucleotide screening using the oligonucleotides:

5' TCCAGATGTTAACTGCTCAC (SEQ ID NO:1) for the light chain, which is complementary to a sequence in the mouse kappa constant region, and 5' CAGGGGCCAGTGGATGGATAGAC (SEQ ID NO:2) for the heavy chain which is complementary to a sequence in the mouse IgG2a constant CH1 domain region. 12 light chain and 9 heavy chain clones were identified and taken for second round screening. Positive clones from the second round of screening were grown up and DNA prepared. The sizes of the gene inserts were estimated by gel electrophoresis and inserts of a size capable of containing a full length cDNA were subcloned into M13 for DNA sequencing.

6. DNA SEQUENCING

Clones representing four size classes for both heavy and light chains were obtained in M13. DNA sequence for the 5' untranslated regions, signal sequences, variable regions and 3' untranslated regions of full length cDNAs [FIGS. 1(*a*) (SEQ ID NO:4) and 2(*a*) (SEQ ID NO:6)] were obtained and the corresponding amino acid sequences predicted [(FIGS. 1(*b*) (SEQ ID NO:5) and 2(*b*) (SEQ ID NO:7)]. In FIG. 1(*a*) the untranslated DNA regions are shown in uppercase, and in both FIGS. 1 (SEQ ID NOS:4 and 5) and 2 (SEQ ID NO:6 and 7) the signal sequences are underlined.

7. CONSTRUCTION OF cDNA EXPRESSION VECTORS

Celltech expression vectors are based on the plasmid pEE6hCMV (ref. 14). A polylinker for the insertion of genes to be expressed has been introduced after the major immediate early promoter/enhancer of the human Cytoaegalovirus (hCMV). Marker genes for selection of the plasmid in transfected eukaryotic cells can be inserted as BamH1 cassettes in the unique BamH1 site of pEE6 hCMV; for instance, the neo marker to provide pEE6 hCMV neo. It is usual practice to insert the neo and gpt markers prior to insertion of the gene of interest, whereas the GS marker is inserted last because of the presence of internal EcoR1 sites in the cassette.

The selectable markers are expressed from the SV40 late promoter which also provides an origin of replications that the vectors can be used for expression in the COS cell transient expression system.

The mouse sequences were excised from the M13 based vectors described above as Ecro1 fragments and cloned into either pEE6-hCMV-neo for the heavy chain and into EE6-hCMV-gpt for the light chain to yield vectors pJA136 and pJA135 respectively.

8. EXPRESSION OF cDNAS IN COS CELLS

Plasmids pJA135 and pJA136 were co-transfected into COS cells and supernatant from the transient expression experiment was shown to contain assembled antibody which bound to T-cell enriched lymphocytes. Metabolic labelling experiments using $^{35}S$ methionine showed expression and assembly of heavy and light chains.

9. CONSTRUCTION OF CHIMERIC GENES

Construction of chimeric genes followed a previously described strategy [Whittle et al (ref. 13)]. A restriction site near the 3' end of the variable domain sequence is identified and used to attach an oligonucleotide adapter coding for the remainder of the mouse variable region and a suitable restriction site for attachment to the constant region of choice.

9.1. LIGHT CHAIN GENE CONSTRUCTION

The mouse light chain cDNA sequence contains an Ava1 site near the 3' end of the variable region [FIG. 1(*a*) (SEQ ID NO:4)]. The majority of the sequence of the variable region was isolated as a 396 bp. EcoR1-Ava1 fragment. An oligonucleotide adapter was designed to replace the remainder of the 3' region of the variable region from the Ava1 site and to include the 5' residues of the human constant region up to and including a unique Nar1 site which had been previously engineered into the constant region.

A Hindlll site was introduced to act as a marker for insertion of the linker.

The linker was ligated to the $V_L$ fragment and the 413 bp EcoR1-Nar1 adapted fragment was purified from the ligation mixture.

The constant region was isolated as an Nar1-BamH1 fragment from an M13 clone NW361 and was ligated with the variable region DNA into an Ecro1/BamH1/C1P pSP65 treated vector in a three way reaction to yield plasmid JA143. Clones were isolated after transformation into *E. coli* and the linker and junction sequences were confirmed by the presence of the Hindlll site and by DNA sequencing.

9.2 LIGHT CHAIN GENE CONSTRUCTION—VERSION 2

The construction of the first chimeric light chain gene produces a fusion of mouse and human amino acid sequences at the variable-constant region junction. In the case of the OKT3 light chain the amino acids at the chimera junction are:

(SEQ ID NO:3)

........Leu-Glu-Ile-Asn-Arg/   -/Thr-Val-Ala        -Ala
            VARIABLE     CONSTANT

This arrangement of sequence introduces a potential site for Asparagine (Asn) linked (N-linked) glycosylation at the V-C junction. Therefore, a second version of the chimeric light chain oligonucleotide adapter was designed in which the threonine (Thr), the first amino acid of the human constant region, was replaced with the equivalent amino acid from the mouse constant region, Alanine (Ala).

An internal Hindlll site was not included in this adapter, to differentiate the two chimeric light chain genes.

The variable region fragment was isolated as a 376 bp EcoR1-Ava1 fragment. The oligonucleotide linker was ligated to Nar1 cut pNW361and then the adapted 396 bp constant region was isolated after recutting the modified pNW361 with EcoR1. The variable region fragment and the modified constant region fragment wore ligated directly into EcoR1/C1P treated pEE6hCMVneo to yield pJA137. Initially all clones examined had the insert in the incorrect orientation. Therefore, the insert was re-isolated and-recloned to turn the insert round and yield plasmid pJA141. Several clones with the insert in the correct orientation were obtained and the adapter sequence of one was confirmed by DNA sequencing

9.3. HEAVY CHAIN GENE CONSTRUCTION
9.3.1. CHOICE OF HEAVY CHAIN GENE ISOTYPE
The constant region isotype chosen for the heavy chain was human IgG4.

9.3.2. GENE CONSTRUCTION
The heavy chain cDNA sequence showed a Ban1 site near the 3' end of the variable region [FIG. 2(a) (SEQ ID NO:6)].

The majority of the sequence of the variable region was isolated as a 426 bp. Ecro1/C1P/Ban fragment. An oligonucleotide adapter was designated to replace the remainder of the 3' region of the variable region from the Ban1 site up to and including a unique Hindlll site which had been previously engineered into the first two amino acids of the constant region.

The linker was ligated to the $V_H$ fragment and the EcoR1-Hindlll adapted fragment was purified from the ligation mixture.

The variable region was ligated to the constant region by cutting pJA91 with EcoR1 and Hind111 removing the intron fragment and replacing it with the $V_H$ to yield pJA142. Clones were isolated after transformation into E. coli JM101 and the linker and junction sequences were confirmed by DNA sequencing. (N.B. The Hindlll site is lost on cloning).

10. CONSTRUCTION OF CHIMERIC EXPRESSION VECTORS
10.1. neo AND gpt VECTORS
The chimeric light chain (version 1) was removed from pJA143 as an EcoR1 fragment and cloned into EcoR1/C1P treated pEE6hCMVneo expression vector to yield pJA145. Clones with the insert in the correct orientation were identified by restriction mapping.

The chimeric light chain (version 2) was constructed as described above.

The chimeric heavy chain gene was isolated from pJA142 as a 2.5 Kbp EcoR1/BamH1 fragment and cloned into the EcoR1/Bcl1/C1P treated vector fragment of a derivative of pEE6hCMVgpt to yield plasmid pJA144.

10.2. GS SEOARATE VECTORS
GS versions of pJA141 and pJA144 were constructed by replacing the neo and gpt cassettes by a BamH1/Sal1/C1P treatment of the plasmids, isolation of the vector fragment and ligation to a GS-containing fragment from the plasmid pRO49 to yield the light chain vector pJA179 and the heavy chain vector pJA180.

10.3. GS SINGLE VECTOR CONSTRUCTION
Single vector constructions containing the cL (chimeric light), cH (chimeric heavy) and GS genes on one plasmid in the order cL-cH-GS, or cH-cL-GS and with transcription of the genes being head to tail e.g. cL>cH>GS were constructed. These plasmids were made by treating pJA179 or pJA180 with BamH1/C1P and ligating in a Bglll/Hindlll hCMV promoter cassette along with either the Hindlll/BamH1 fragment from pJA141 into pJA180 to give the cH-cL-GS plasmid pJA182 or the Hindlll/BamH1 fragment from pJA144 into pJA179 to give the cL-cH-GS plasmid pJA181.

11. EXPRESSION OF CHIMERIC GENES
11.1. EXPRESSION IN COS CELLS
The chimeric antibody plasmid pJA145 (cL) and pJA144 (cH) were co-transfected into COS cells and supernatant from the transient expression experiment was shown to contain assembled antibody which bound to the HUT 78 human T-cell line. Metabolic labelling experiments using $^{35}S$ methionine showed expression and assembly of heavy and light chains. However the light chain mobility seen on reduced gels suggested that the potential glycosylation site was being glycosylated. Expression in COS cells in the presence of tunicamycin showed a reduction in size of the light chain to that shown for control chimeric antibodies and the OKT3 mouse light chain. Therefore JA141 was constructed and expressed. In this case the light chain did not show an aberrant mobility or a size shift in the presence or absence of tunicamycin. This second version of the chimeric light chain, when expressed in association with chimeric heavy (cH) chain, produced antibody which showed good binding to HUT 78 cells. In both cases antigen binding was equivalent to that of the mouse antibody.

11.2 EXPRESSION IN CHINESE HAMSTER OVARY (CEO) CELLS
Stable cell lines have been prepared from plasmids PJA141/pJA144 and from pJA179/pJA180, pJA181 and pJA182 by transfection into CHO cells.

12. CDR-GRAFTING
The approach taken was to try to introduce sufficient mouse residues into a human variable region framework to generate antigen binding activity comparable to the mouse and chimeric antibodies.

12.1. VARIABLE REGION ANALYSIS
From an examination of a small database of structures of antibodies and antigen-antibody complexes it is clear that only a small number of antibody residues make direct contact with antigen. Other residues may contribute to antigen binding by positioning the contact residues in favourable configurations and also by inducing a stable packing of the individual variable domains and stable interaction of the light and heavy chain variable domains.

The residues chosen for transfer can be identified in a number of ways:
  (a) By examination of antibody X-ray crystal structures the antigen binding surface can be predominantly located on a series of loops, three per domain, which extend from the B-barrel framework.
  (b) By analysis of antibody variable domain sequences regions of hypervariability [termed the Complementarity Determining Regions (CDRs) by Wu and Kabat (ref. 5)] can be identified. In the most but not all cases these CDRs correspond to, but extend a short way beyond, the loop regions noted above.
  (c) Residues not identified by (a) and (b) may contribute to antigen binding directly or indirectly by affecting antigen binding site topology, or by inducing a stable packing of the individual variable domains and stabilizing the inter-variable domain interaction. These residues may be identified either by superimposing the sequences for a given antibody on a known structure and looking at key residues for their contribution, or by sequence alignment analysis and noting "idiosyncratic" residues followed by examination of their structural location and likely effects.

12.1.1. LIGHT CHAIN
FIG. 3 (SEQ ID NO:29, 8 and 9) shows an alignment of sequences for the human framework region RE1 (SEQ ID NO:8 and 9) and the OKT3 light variable region (SEQ ID NO:29). The structural loops (LOOP) and CDRs (KABAT) believed to correspond to the antigen binding region are marked. Also marked are a number of other residues which may also contribute to antigen binding as described in 13.1(c).

Above the sequence in FIG. 3 (SEQ ID NO:29, 8 and 9) the residue type indicates the spatial location of each residue side chain, derived by examination of resolved structures from X-ray crystallography analysis.

The key to this residue type designation is as follows:

| | |
|---|---|
| N | near to CDR (From X-ray Structures) |
| P | Packing |
| S | Surface |
| I | Interface |
| | Packing/Part Exposed |
| B | Buried Non-Packing |
| E | Exposed |
| * | Interface |
| ? | Non-CDR Residues which may require to be left as Mouse sequence. |

Residues underlined in FIG. 3 (SEQ ID NO:29, 8 and 9) are amino acids. RE1 (SEQ ID NO:8 and 9) was chosen as the human framework because the light chain is a kappa chain and the kappa variable regions show higher homology with the mouse sequences than a lambda light variable region, e.g. KOL (SEQ ID NO:10) (see below). RE1 (SEQ ID NO:8 and 9) was chosen in preference to another kappa light chain because the X-ray structure of the light chain has been determined so that a structural examination of individual residues could be made.

12.1.2. HEAVY CHAIN

Similarly FIG. 4 shows an alignment of sequences for the human framework region KOL (SEQ ID NO:10) and the OKT3 (SEQ ID NO:30) heavy variable region. The structural loops and CDRs believed to correspond to the antigen binding region are marked. Also marked are a number of other residues which may also contribute to antigen binding as described in 12.1(c). The residue type key and other indicators used in FIG. 4 are the same as those used in FIG. 3. KOL (SEQ ID NO:10) was chosen as the heavy chain framework because the X-ray structure has been determined to a better resolution than, for example, NEWM and also the sequence alignment of OKT3 heavy variable region (SEQ ID NO:30) showed a slightly better homology to KOL (SEQ ID NO:10) than to NEWM.

12.2. DESIGN OF VARIABLE GENES

The variable region domains were designed with mouse variable region optimal codon usage [Grantham and Perrin (ref. 15)] and used the B72.3 signal sequences [Whittle et al (ref. 13)]. The sequences were designed to be attached to the constant region in the same way as for the chimeric genes described above. Some constructs contained the "Kozak consensus sequence" [Kozak (ref. 16)] directly linked to the 5' of the signal sequence in the gene. This sequence motif is believed to have a beneficial role in translation initiation in eukaryotes.

12.3. GENE CONSTRUCTION

To build the variable region, various strategies are available. The sequence may be assembled by using oligonucleotides in a manner similar to Jones et al (ref. 17) or by simultaneously replacing all of the CDRs or loop regions by oligonucleotide directed site specific mutagenesis in a manner similar to Verhoeyen et al (ref. 2).

Both strategies were used and a list of constructions is set out in Tables 1 and 2 and FIGS. 4 and 5. It was noted in several cases that the mutaqenesis approach led to deletions and rearrangements in the gene being remodelled, while the success of the assembly approach was very sensitive to the quality of the oligonucleotides.

13. CONSTRUCTION OF EXPRESSION VECTORS

Genes were isolated from M13 or SP65 based intermediate vectors and cloned into pEE6hCMVneo for the light chains and pEE6hCMVgpt for the heavy chains in a manner similar to that for the chimeric genes as described above.

TABLE 1

CDR-GRAFTED GENE CONSTRUCTS

| CODE | MOUSE SEQUENCE CONTENT | METHOD OF CONSTRUCTION | KOZAK SEQUENCE − | KOZAK SEQUENCE + |
|---|---|---|---|---|
| LIGHT CHAIN ALL HUMAN FRAMEWORK RE1 | | | | |
| 121 | 26–32, 50–56, 91–96 inclusive | SDM and gene assembly | + | n.d. |
| 121A | 26–32, 50–56, 91–96 inclusive +1, 3, 46, 47 | Partial gene assembly | n.d. | + |
| 121B | 26–32, 50–56, 91–96 inclusive +46, 47 | Partial gene assembly | n.d. | + |
| 221 | 24–24, 50–56, 91–96 inclusive | Partial gene assembly | + | + |
| 221A | 24–34, 50–56, 91–96 inclusive +1, 3, 46, 47 | Partial gene assembly | + | + |
| 221B | 24–34, 50–56, 91–96 inclusive +1, 3 | Partial gene assembly | + | + |
| 221C | 24–34, 50–56, 91–96 inclusive | Partial gene assembly | + | + |
| HEAVY CHAIN ALL HUMAN FRAMEWORK KOL | | | | |
| 121 | 26–32, 50–56, 95–100B inclusive | Gene assembly | n.d. | + |
| 131 | 26–32, 50–58, 95–100B inclusive | Gene assembly | n.d. | + |
| 141 | 26–32, 50–65, 95–100B inclusive | Partial gene assembly | + | n.d. |
| 321 | 26–35, 50–56, 95–100B inclusive | Partial gene assembly | + | n.d. |

TABLE 1-continued

CDR-GRAFTED GENE CONSTRUCTS

| CODE | MOUSE SEQUENCE CONTENT | METHOD OF CONSTRUCTION | KOZAK SEQUENCE − | KOZAK SEQUENCE + |
|---|---|---|---|---|
| 331 | 26–35, 50–58, 95–100B inclusive | Partial gene assembly | + | |
| | | Gene assembly | | + |
| 341 | 26–35, 50–65, 95–100B inclusive | SDM | + | |
| | | Partial gene assembly | | + |
| 341A | 26–35, 50–65, 95–100B inclusive +6, 23, 24, 48, 49, 71, 73, 76, 78, 88, 91 (+63 − human) | Gene assembly | n.d. | + |
| 341B | 26–35, 50–65, 95–100B inclusive +48, 49, 71, 73, 76, 78, 88, 91 (+63 + human) | Gene assembly | n.d. | + |

KEY
n.d. not done
SDM Site directed mutagenesis
Gene assembly Variable region assembled entirely from oligonucleotides
Partial gene assembly Variable region assembled by combination of restriction fragments either from other genes originally created by SDM and gene assembly or by oligonucleotide assembly of part of the variable region and reconstruction with restriction fragments from ther genes originally created by SDM and gene assembly

14. EXPRESSION OF CDR-GRAFTED GENES 14.1. PRODUCTION OF ANTIBOBY CONSISTING OF GRAFTED LIGHT (gL) CHAINS WITH MOUSE HEAVY (mH) OR CHIMERIC HEAVY (cH) CHAINS

All gL chains, in association with mH or cH produced reasonable amounts of antibody.

Insertion of the Kozak consensus sequence at a position 5' to the ATG (kgL constructs) however, led to a 2–5 fold improvement in net expression. Over an extended series of experiments expression levels were raised from approximately 200 ng/ml to approximately 500 ng/ml for kgL/cH or kgL/mH combinations.

When direct binding to antigen on HUT 78 cells was measured, a construct designed to include mouse sequence based on loop length (gL121) did not lead to active antibody in association with mH or cH. A construct designed to include mouse sequence based on Kabat CDRs (gL221) (SEQ ID NO:25) demonstrated some weak binding in association with mH or cH. However, when framework residues 1, 3, 46, 47 were changed from the human to the murine OKT3 equivalents based on the arguments outlined in Section 12.1 antigen binding was demonstrated when both of the new constructs, which were termed 121A and 221A were co-expressed with cH. When the effects of these residues were examined in more detail, it appears that residues 1 and 3 are not major contributing residues as the product of the gL221B gene (SEQ ID NO:29) shows little detectable binding activity in association with cH. The light chain product of gL221C (SEQ ID NO:28), in which mouse sequences are present at 46 and 47, shows good binding activity in association with cH.

14.2 PRODUCTION OF ANTIBODY CONSISTING OF GRAFTED HEAVY (gH) CHAINS WITH MOUSE LIGHT (mL) OR CHIMERIC LIGHT (cL) CHAINS

Expression of the gH genes proved to be more difficult to achieve than for gL. First, inclusion of the Kozak sequence appeared to have no marked effect on expression of gH genes. Expression appears to be slightly improved but not to the same degree as seen for the grafted light chain.

Also, it proved difficult to demonstrate production of expected quantities of material when the loop choice (amino acid 26–32) for CDR1 is used, e.g. gH121, 131, 141 and no conclusions can be drawn about these constructs.

Moreover, co-expression of the gH341 gene (SEQ ID NO:11) with cL or mL has been variable and has tended to produce lower amounts of antibody than the cH/cL or mH/mL combinations. The alterations to gH341 (SEQ ID NO:11) to produce gH341A (SEQ ID NO:12) and gH341B (SEQ ID NO:21) lead to improved levels of expression.

This may be due either to a general increase in the fraction of mouse sequence in the variable region, or to the alteration at position 63 where the residue is returned to the human amino acid Valine (Val) from Phenylalanine (Phe) to avoid possible internal packing problems with the rest of the human framework. This arrangement also occurs in gH331 and gH321.

When gH321 or gH331 were expressed in association with cL, antibody was produced but antibody binding activity was not detected.

When the more conservative gH341 gene (SEQ ID NO:11) was used antigen binding could be detected in association with cL or mL, but the activity was only marginally above the background level.

When further mouse residues were substituted based an the arguments in 12.1, antigen binding could be clearly demonstrated for the antibody produced when kgH341A and kgH341B were expressed in association with cL.

14.3 PRODUCTION OF FULLY CDR-GRAFTED ANTIBODY

The kgL221A gene was co-expressed with kgH341, kgH341A or kgH341B. For the combination kgH221A/kgH341 very little material was produced in a normal COS cell expression.

For the combinations kgL221A/kgH341A or kgH221A/kgH341B amounts of antibody similar to gL/cg was produced.

In several experiments no antigen binding activity could be detected with kgL221A/gH341 or kgH221A/kgH341 combinations, although expression levels were very low.

Antigen binding was detected when kgL221A/kgH341A or kgH221A/kgH341B combinations were expressed. In the case of the antibody produced from the kgL221A/kgH341A combination the antigen binding was very similar to that of the chimeric antibody.

An analysis of the above results is given below.

15. DISCUSSION OF CDR-GRAFTING RESULTS

In the design of the fully humanised antibody the aim was to transfer the minimum number of mouse amino acids that would confer antigen binding onto a human antibody framework.

15.1. LIGHT CHAIN

15.1.1. EXTENT OF THE CDRs

For the light chain the regions defining the loops known from structural studies of other antibodies to contain the antigen contacting residues, and this hypervariable sequences defined by Kabat et al (refs. 4 and 5) as Complementarity Determining Regions (CDRs) are equivalent for CDR2. For CDR1 the hypervariable region extends from residues 24–34 inclusive while the structural loop extends from 26–32 inclusive. In the case of OKT3 (SEQ ID NO:5) there is only one amino acid difference between the two options, at amino acid 24, where the mouse sequence is a serine and the human framework RE has glutamine. For CDR3 the loop extends from residues 91–96 inclusive while the Kabat hypervariability extends from residues 89–97 inclusive. For OKT3 amino acids 89, 90 and 97 are the same between OKT3 and RE1 (FIG. 3) (SEQ ID NO:29, 8 and 9). When constructs based on the loop choice for CDR1 (gL121) and the Kabat choice (gL221) were made and co-expressed with mH or cH no evidence for antigen binding activity could be found for gL121, but trace activity could be detected for the gL221, suggesting that a single extra mouse residue in the grafted variable region could have some detectable effect. Both gene constructs were reasonably well expressed in the transient expression system.

15.1.2. FRAMEWORK RESIDUES

The remaining framework residues were then further examined, in particular amino acids known from X-ray analysis of other antibodies to be close to the CDRs and also those amino acids which in OKT3 showed differences from the consensus framework for the mouse subgroup (subgroup VI) to which OKT3 shows most homology. Four positions 1, 3, 46 and 47 were identified and their possible contribution was examined by substituting the mouse amino acid for the human amino acid at each position. Therefore gL221A (gL221+D1Q, Q3V, L46R, L47W, see FIG. 3 and Table 1) was made, cloned in EE6hCMVneo and co-expressed with cH (PJA144). The resultant antibody was well expressed and showed good binding activity. When the related genes gL221B (gL221+D1Q, Q3V) and gL221C (SEQ ID NO:28) (gL221+L46R, L47W) were made and similarly tested, while both genes produced antibody when co-expressed with cH, only the gL221C/cH combination showed good antigen binding. When the gL121A (gL121+D1Q, Q3V, L46R, L47W) gene was made and co-expressed with cH, antibody was produced which also bound to antigen.

15.2. HEAVY CHAIN

15.2.1. EXTENT OF THE CDRs

For the heavy chain the loop and hypervariability analyses agree only in CDR3. For CDR1 the loop region extends from residues 26–32 inclusive whereas the Rabat CDR extends from residues 31–35 inclusive. For CDR2 the loop region is from 50–58 inclusive while the hypervariable region covers amino acids 50–65 inclusive. Therefore humanized heavy chains were constructed using the framework from antibody KOL and with various combinations of these CDR choices, including a shorter choice for CDR2 of 50–56 inclusive as there was some uncertainty as to the definition of the end point for the CDR2 loop around residues 56 to 58. The genes were co-expressed with mL or cL initially. In the case of the gH genes with loop choices for CDR1 e.g. gH121, gH131, gH141 very little antibody was produced in the culture supernatants. As no free light chain was detected it was presumed that the antibody was being made and assembled inside the cell but that the heavy chain was aberrant in some way, possibly incorrectly folded, and therefore the antibody was being degraded internally. In some experiments trace amounts of antibody could be detected in $^{35}S$ labelling studies.

As no net antibody was produced, analysis of these constructs was not pursued further.

When, however, a combination of the loop choice and the Kabat choice for CDR1 was tested (mouse amino acids 26–35 inclusive) and in which residues 31 (Ser to Arg), 33 (Ala to Thr), and 35 (Tyr to His) were changed from the human residues to the mouse residue and compared to the first series, antibody was produced for gH321, kgH331 and kgH341 when co-expressed with cL. Expression was generally low and could not be markedly improved by the insertion of the Kozak consensus sequence 5' to the ATG of the signal sequence of the gene, as distinct from the case of the gL genes where such insertion led to a 2–5 fold increase in net antibody production. However, only in the case of gH341/mL or kgH341/cL could marginal antigen binding activity be demonstrated. When the kgH341 gene was co-expressed with kgL221A (SEQ ID NO:26), the net yield of antibody was too low to give a signal above the background level in the antigen binding assay.

15.2.2. FRAMEWORK RESIDUES

As in the case of the light chain the heavy chain frameworks were re-examined. Possibly because of the lower initial homology between the mouse and human heavy variable domains compared to the light chains, more amino acid positions proved to be of interest. Two genes kgH341A and kgH341B were constructed, with 11 or 8 human residues respectively substituted by mouse residues compared to gH341, and with the CDR2 residue 63 returned to the human amino acid potentially to improve domain packing. Both showed antigen binding when combined with cL or kgL221A, the kgH341A gene with all 11 changes appearing to be the superior choice.

15.3 INTERIM CONCLUSIONS

It has been demonstrated, therefore, for OKT3 that to transfer antigen binding ability to the humanized antibody, mouse residues outside the CDR regions defined by the Kabat hypervariability or structural loop choices are required for both the light and heavy chains. Fewer extra residues are needed for the light chain, possibly due to the higher initial homology between the mouse and human kappa variable regions.

Of the changes seven (1 and 3 from the light chain and 6, 23, 71, 73 and 76 from the heavy chain) are predicted from a knowledge of other antibody structures to be either partly exposed or on the antibody surface. It has been shown here that residues 1 and 3 in the light chain are not absolutely required to be the mouse sequence; and for the heavy chain the gH341B heavy chain in combination with the 221A light chain generated only weak binding activity. Therefore the presence of the 6, 23 and 24 changes are important to maintain a binding affinity similar to that of the murine antibody. It was important, therefore, to further study the individual contribution of othe other 8 mouse residues of the kgH341A gene compared to kgH341.

16. FURTHER CDR-GRAFTING EXPERIMENTS

Additional CDR-grafted heavy chain genes were prepared substantially as described above. With reference to Table 2 the further heavy chain genes were based upon the gh341 (plasmid pJA178) and gH341A (plasmid pJA185) (SEQ ID NO:12) with either mouse OKT3 or human KOL residues at 6, 23, 24, 48, 49, 63, 71, 73, 76, 78, 88 and 91, as indicated. The CDR-grafted light chain genes used in these further experiments were gL221 (SEQ ID NO:25), gL221A (SEQ ID NO:26), gL221B (SEQ ID NO:27) and gL221C (SEQ ID NO:28) as described above.

TABLE 2

OKT3 HEAVY CHAIN CDR GRAFTS 1. gH341 and derivatives

| RES NUM | 6 | 23 | 24 | 48 | 49 | 63 | 71 | 73 | 76 | 78 | 88 | 91 | |
|---|---|---|---|---|---|---|---|---|---|---|---|---|---|
| OKT3vh | Q | K | A | I | G | F | T | K | S | A | A | Y | |
| gH341 | E | S | S | V | A | F | R | N | N | L | G | F | JA178 |
| gH341A | Q | K | A | I | G | V | T | K | S | A | A | Y | JA185 |
| gH341E | Q | K | A | I | G | V | T | K | S | A | G | G | JA198 |
| gH341* | Q | K | A | I | G | V | T | K | N | A | G | F | JA207 |
| gH341* | Q | K | A | I | G | V | R | N | N | A | G | F | JA209 |
| gH341D | Q | K | A | I | G | V | T | K | N | L | G | F | JA197 |
| gH341* | Q | K | A | I | G | V | R | N | N | L | G | F | JA199 |
| gH341C | Q | K | A | V | A | F | R | N | N | L | G | F | JA184 |
| gH341* | Q | S | A | I | G | V | T | K | S | A | A | Y | JA203 |
| gH341* | E | S | A | I | G | V | T | K | S | A | A | Y | JA205 |
| gH341B | E | S | S | I | G | V | T | K | S | A | A | Y | JA183 |
| gH341* | Q | S | A | I | G | V | T | K | S | A | G | F | JA204 |
| gH341* | E | S | A | I | G | V | T | K | S | A | G | F | JA206 |
| gH341* | Q | S | A | I | G | V | T | K | N | A | G | F | JA208 |
| KOL | E | S | S | V | A |   | R | N | N | L | G | F | |

(SEQ ID NO: 30, 10 and 11–24)
OKT3 LIGHT CHAIN CDR GRAFTS 2. gL221 and derivatives

| RES NUM | 1 | 2 | 46 | 47 | |
|---|---|---|---|---|---|
| OKT3vl | Q | V | R | W | |
| GL221 | D | Q | L | L | DA221 |
| gL221A | Q | V | R | W | DA221A |
| gL221B | Q | V | L | L | DA221B |
| GL221C | D | Q | R | W | DA221C |
| RE1 | D | Q | L | L | |

(SEQ ID NO: 29, 8, 9 and 25–28)

MURINE RESIDUES ARE UNDERLINED

The CDR-grafted heavy and light chain genes were co-expressed in COS Cells either with one another in various combinations but also with the corresponding marine and chimeric heavy and light chain genes substantially as described above. The resultant antibody products were then assayed in binding and blocking assays with HPB-ALL cells as described above.

Figure 8:
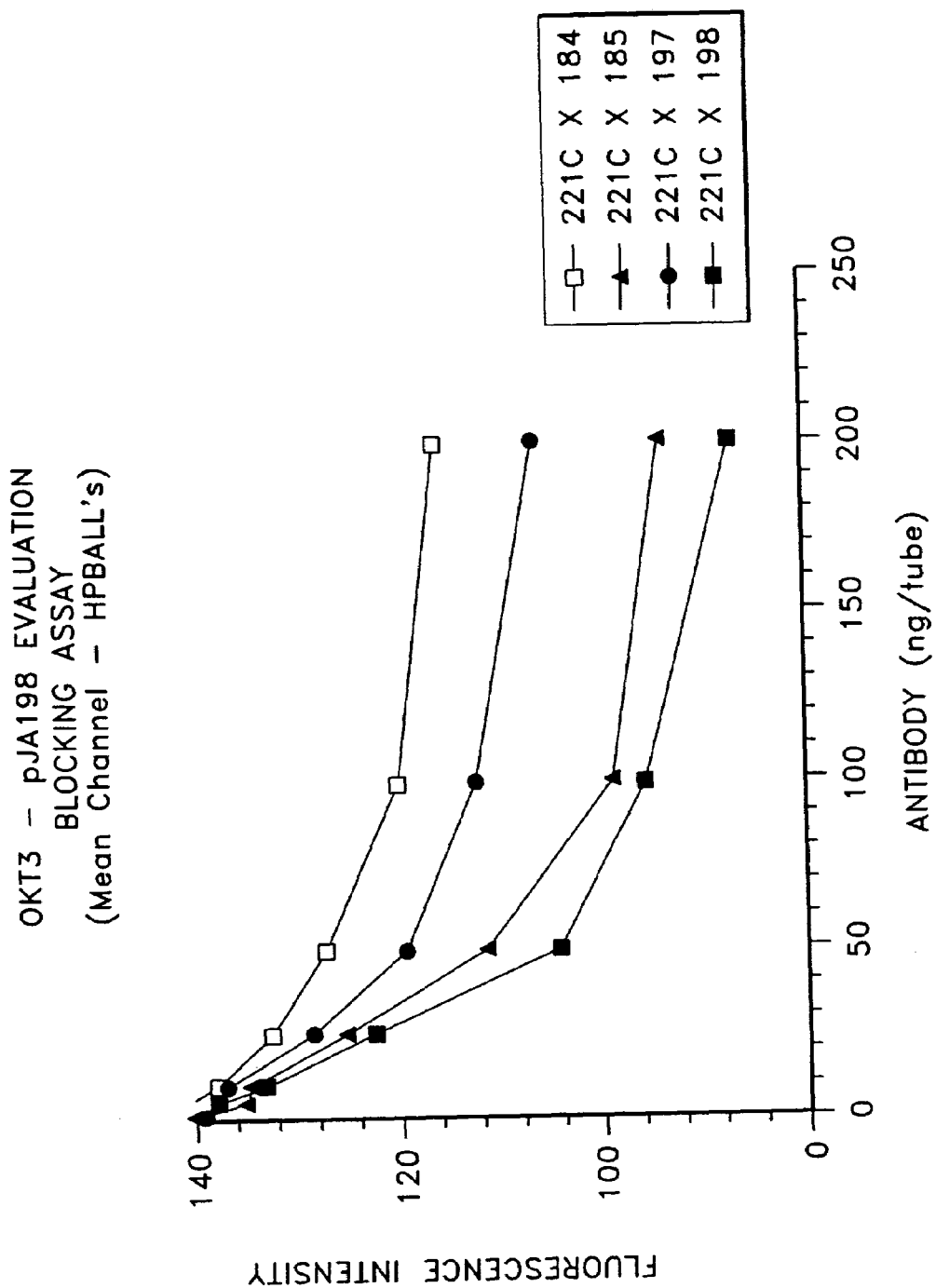
FIG. 8 shows a graph of blocking assay results for various grafted OKT3 antibodies.
Figure 9:
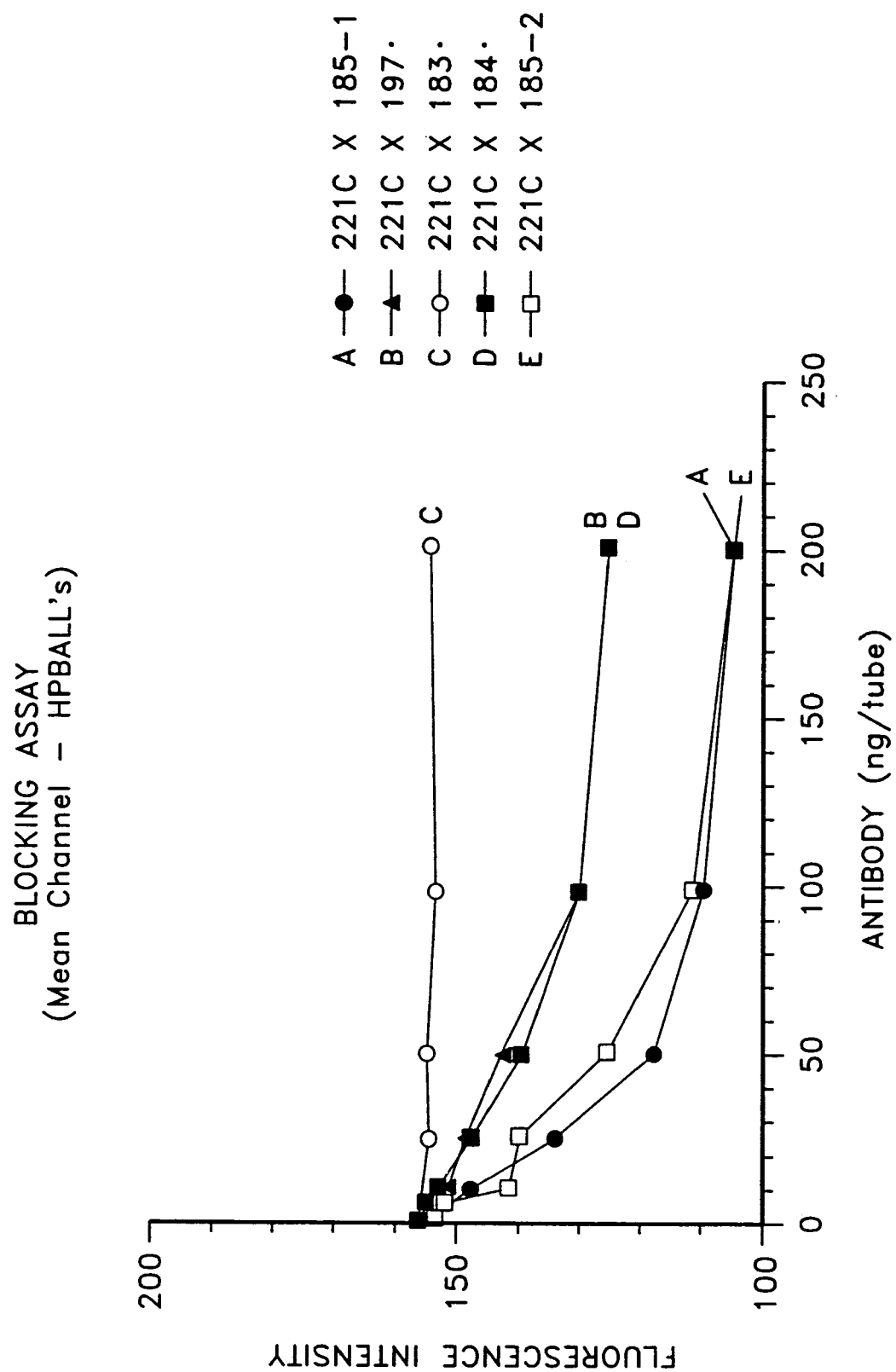
FIG. 9 shows a similar graph of blocking assay results.
Figure 10A:
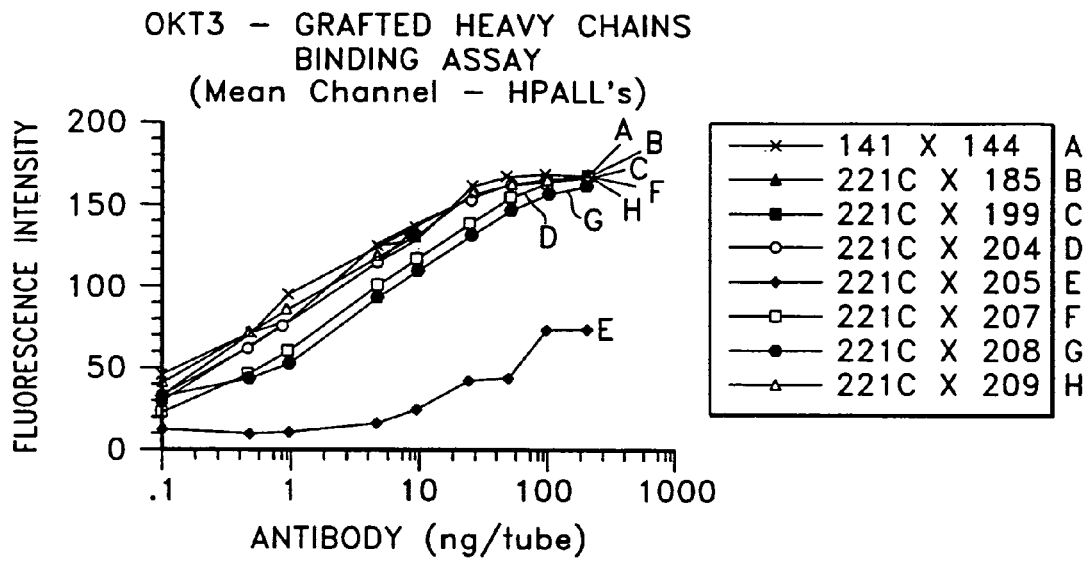
FIGS. 10a and b show similar graphs for both binding assay and blocking assay results.
Figure 10B:
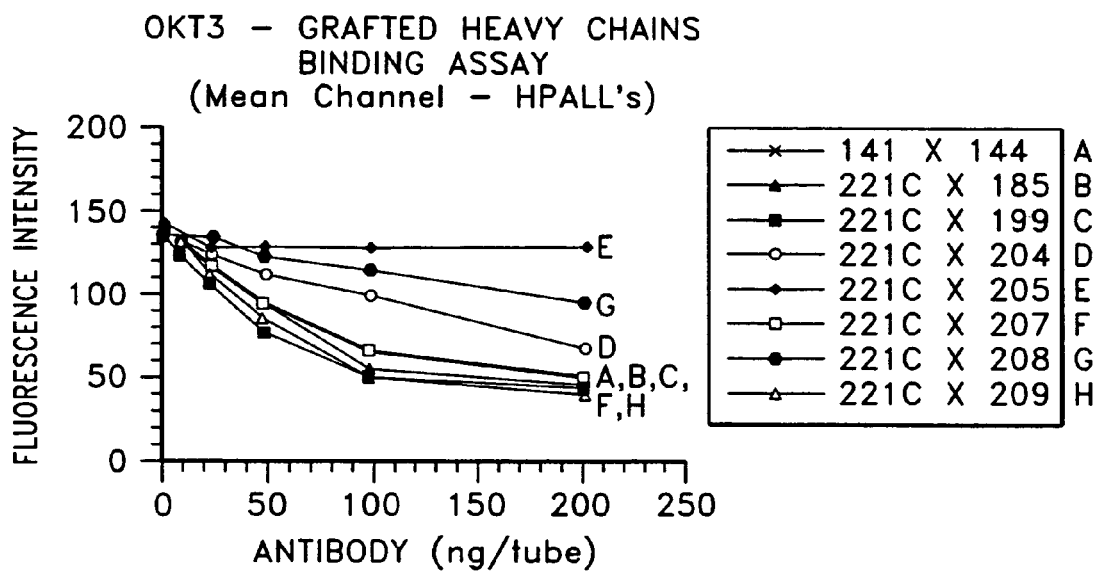
Figure 11A:
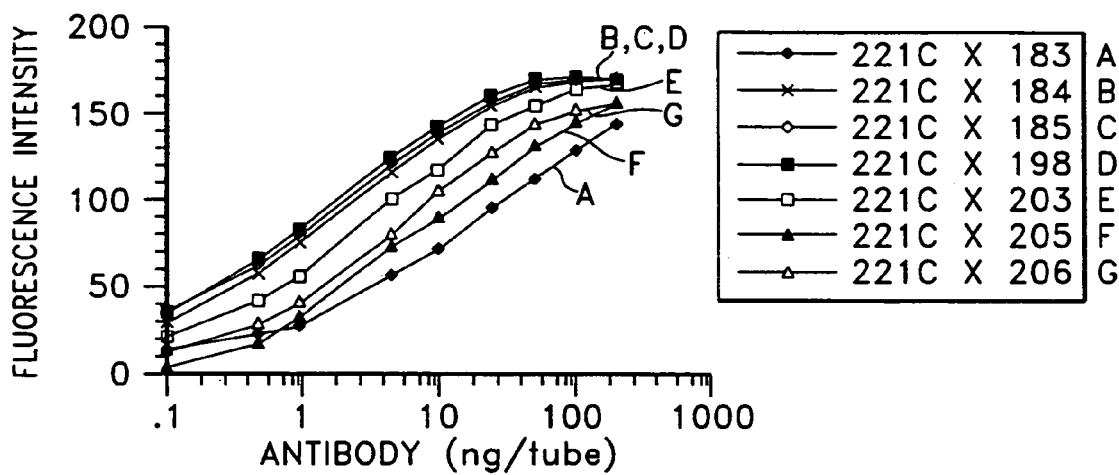
FIGS. 11a and b show further similar graphs for both binding assay and blocking assay results.
Figure 11B:
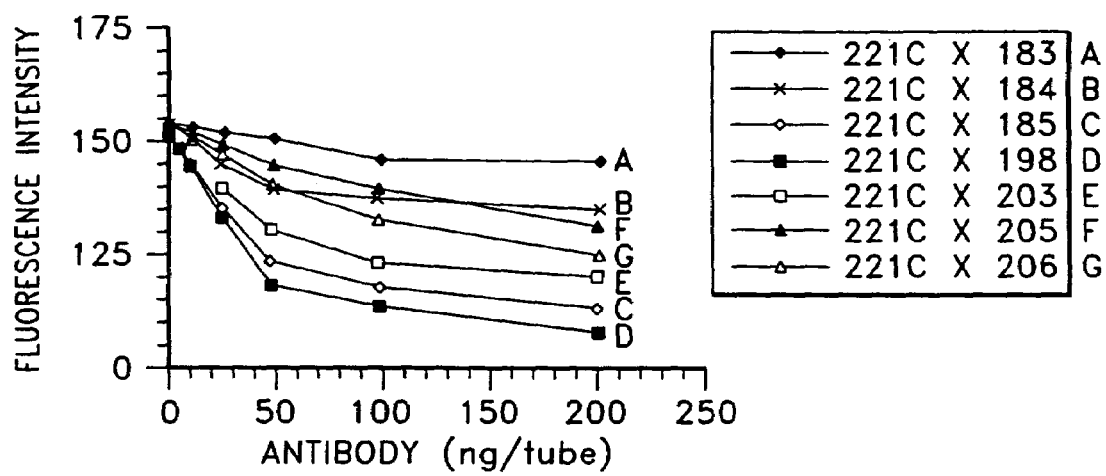

The results of the assays for various grafted heavy chains co-expressed with the gL221C light chain (SEQ ID NO:28) are given in FIGS. 7 and 8 (for the JA184, JA185, JA197 and JA198 constructs—see Table 2), in FIG. 9 (for the JA183, JA184, JA185 and JA197 constructs) in FIGS. 10a and b (for the chimeric, JA185, JA199, JA204, JA205, JA207, JA208 and JA209 constructs) and in FIGS. 11a and b (for the JA183, JA184, JA185, JA198, JA203, JA205 and JA206 constructs).

Figure 12:
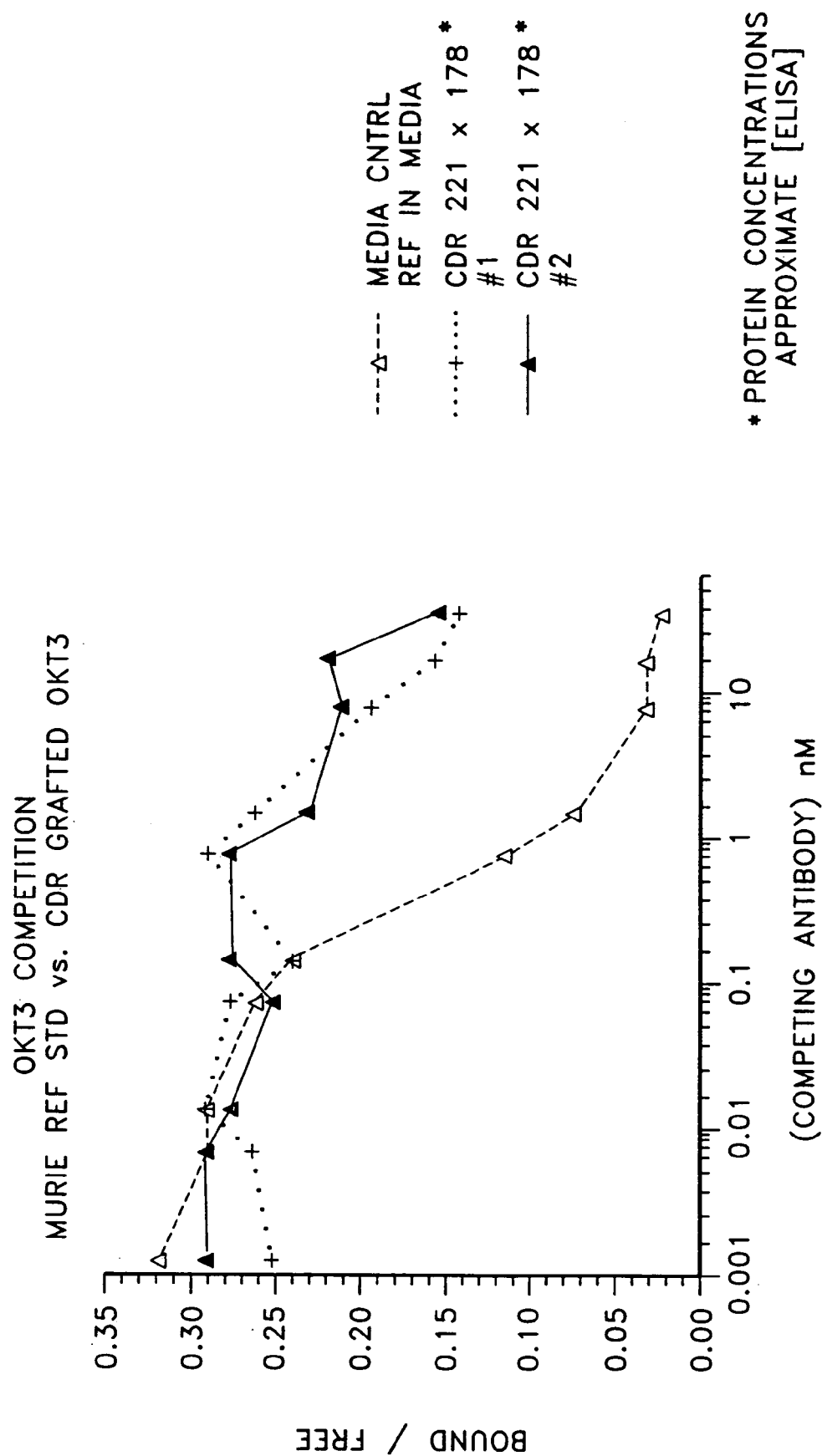
FIG. 12 shows a graph of competition assay results for a minimally grafted OKT3 antibody compared with the OKT3 murine reference standard.
Figure 13:
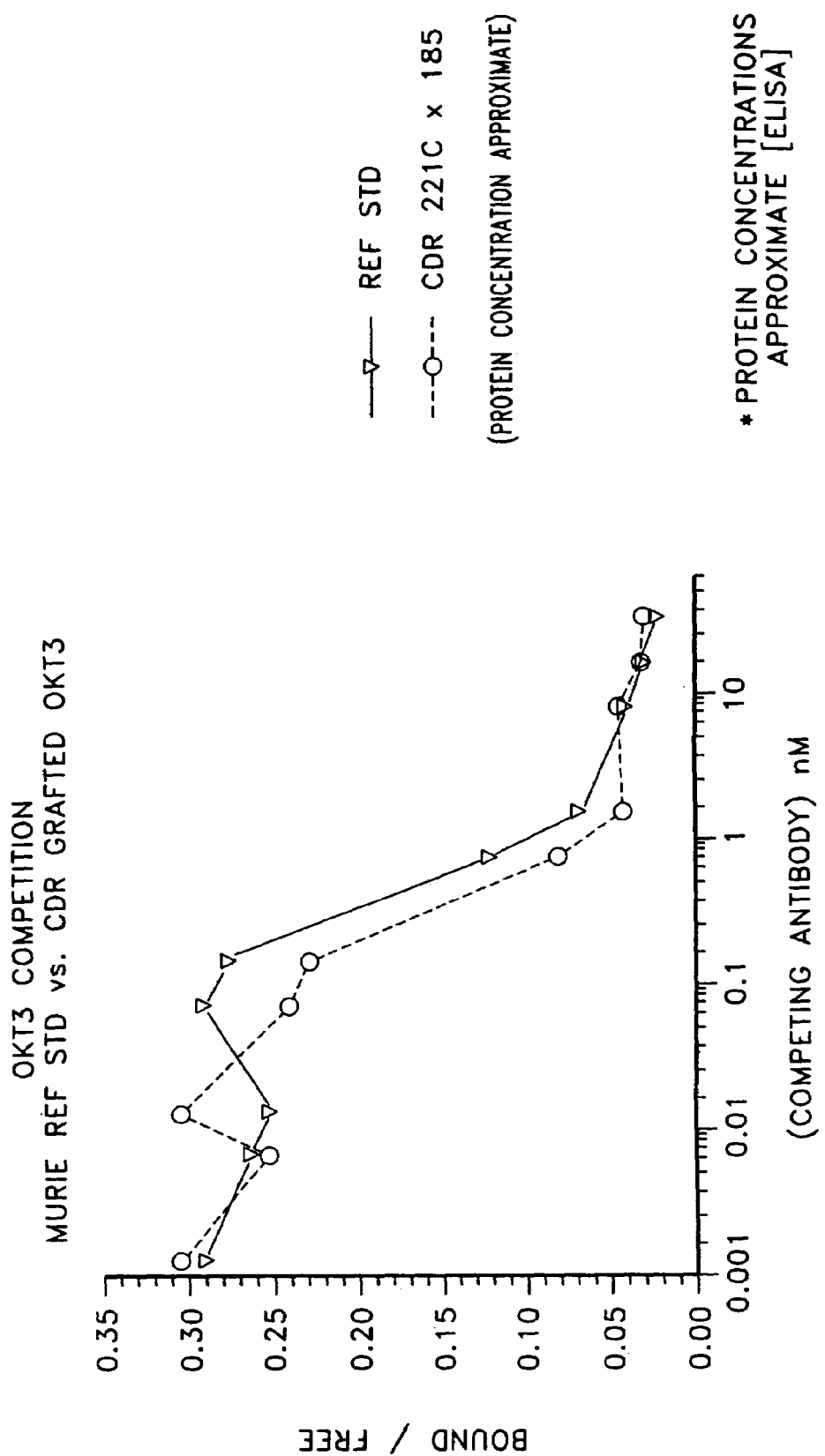
FIG. 13 shows a similar graph of competition assay results comparing a fully grafted OKT3 antibody with the murine reference standard.

The basic grafted product without any human to murine changes in the variable frameworks, i.e. gL221 (SEQ ID NO:25) co-expressed with gh341 (JA178) (SEQ ID NO:11), and also the "fully grafted" product, having most human to marine changes in the grafted heavy chain framework, i.e. gL221C (SEQ ID NO:28) co-expressed with gh341A (JA185) (SEQ ID NO:12), were assayed for relative binding affinity in a competition assay against murine OKT3 reference standard, using HPB-ALL cells. The assay used was as described above in section 3.3. The results obtained are given in FIG. 12 for the basic grafted product and in FIG. 13 for the fully grafted product. These results indicate that the basic grafted product has negligible binding ability as compared with the OKT3 murine reference standard; whereas the "fully grafted" product has a binding ability very similar to that of the OKT3 urine reference standard.

The binding and blocking assay results indicate the following:

The JA198 and JA207 constructs appear to have the best binding characteristics and similar binding abilities, both substantially the same as the chimeric and fully grafted gH341A products. This indicates that positions 88 and 91 and position 76 are not highly critical for maintaining the OKT3 binding ability; whereas at least same of positions 6, 23, 24, 48, 49, 71, 73 and 78 are more important.

This is borne out by the finding that the JA209 and JA199, although of similar binding ability to one another, are of lower binding ability than the JA198 and JA207 constructs. This indicates the importance of having mouse residues at positions 71, 73 and 78, which are either completely or partially human in the JA199 and JA209 constructs respectively.

Moreover, on comparing the results obtained for the JA205 and JA183 constructs it is seen that there is a decrease in binding going from the JA205 to the JA183 constructs. This indicates the importance of retaining a mouse residue at position 23, the only position changed between JA205 and JA183.

These and other results lead us to the conclusion that of the 11 mouse framework residues used in the gH341A (JA185) construct, it is important to retain mouse residues at all of positions 6, 23, 24, 48 and 49, and possibly for maximize binding affinity at 71, 73 and 78.

Similar Experiments were carried out to CDR-graft a number of the rodent antibodies including antibodies having specificity for CD4 (OKT4), ICAM-1 (R6-5), TAG72 (B72.3), and TNFα(61E71, 101.4, hTNF1, hTNF2 and hTNF3).

EXAMPLE 2

CDR-Grafting of a Murine Anti-CD4 T Cell Receptor Antibody, OKT4A

Anti OKT4A CDR-grafted heavy and light chain genes were prepared, expressed and tested substantially as described above in Example 1 for CDR-grafted OKT3. The CDR grafting of OKT4A is described in detail in Ortho patent application PCT/GB 90 . . . of even date herewith entitled "Humanized Antibodies". The disclosure of this Ortho patent application PCT/GB 90 . . . is incorporated herein by reference. A number of CDR-grafted OKT4 antibodies have been prepared. Presently the CDR-grafted OKT4A of choice is the combination of the grafted light chain LCDR2 and the grafted heavy chain HCDR10.

The Light Chain

The human acceptor framework used for the grafted light chains was RE1 (SEQ ID NO:8 and 9). The preferred LCDR2 light chain has human to mouse changes at positions 33, 34, 38, 49 and 89 in addition to the structural loop CDRA. Of these changed positions, positions 33, 34 and 89 fall within the preferred extended CDRs of the present invention (positions 33 and 34 in CDR1 and position 89 in CDR3).

The human to marine changes at positions 38 and 49 corresponds to positions at which the amino acid residues are preferably donor murine amino acid residues in accordance with the present invention.

A comparison of the amino acid sequences of the donor murine light chain variable domain and the RE1 human acceptor light chain variable further reveals that the murine and human residues are identical at all of positions 46, 48 and 71 and at all of positions 2, 4, 6, 35, 36, 44, 47, 62, 64–69, 8:5, 87, 98, 99 and 101 and 102. However the amino acid residue at position 58 in LCDR2 is the human RE1 framework residue in the mouse OKT4 residue as would be preferred in accordance with the present invention.

The Heavy Chain

The human acceptor framework used for the grafted heavy chains was KOL (SEQ ID NO:10).

The preferred CDR graft HCDR10 heavy chain has human to mouse changes at positions 24, 35, 57, 58, 60, 88 and 91 in addition to the structural loop CDRs.

Of these positions, positions 35 (CDR1) and positions 57, 58 and 60 (CDR2) fall within the preferred extended CDRs of the present invention. Also the human to mouse change at position 24 corresponds to a position at which the amino acid residue is a donor murine residue in accordance with the present invention. Moreover, the human to mouse changes at positions 88 and 91 correspond to positions at which the amino acid residues are optionally donor murine residues.

Moreover, a comparison of the marine OKT4A and human KOL heavy chain variable amino acid sequences reveals that the murine and human residues are identical at all of positions 23, 49, 71, 73 and 78 and at all of positions 2, 4, 6, 25, 36, 37, 39, 47, 48, 93, 94, 103, 104, 106 and 107.

Thus the OKT4A CDR-grafted heavy chain HCDR10 corresponds to a particularly preferred embodiment according to the present invention.

EXAMPLE 3

CDR-Grafting of an Anti-Mucin Specific Murine Antibody, B72.3

The cloning of the genes coding for the anti-mucin specific murine monoclonal antibody B72.3 and the preparation of 372.3 mouse-human chimeric antibodies has been described previously (ref. 13 and WO 89/01783). CDR-grafted versions of B72.3 were prepared as follows.

(a) 372.3 Light Chain

CDR-grafting of this light chain was accomplished by direct transfer of the murine CDRs into the framework of the human light chain RE1. The regions transferred were:

| CDR Number | Residues |
|---|---|
| 1 | 24–34 |
| 2 | 50–56 |
| 3 | 90–96 |

The activity of the resulting grafted light chain was assessed by co-expression in COS cells, of genes for the combinations:

B72.3 cH/B72.3 cL and

B72.3 cH/B72.3 gL

Supernatants were assayed for antibody concentration and for the ability to bind to microtitre plates coated with mucin. The results obtained indicated that, in combination with the B72.3 cH chain, B72.3 cL and B72.3 gL had similar binding properties.

Comparison of the murine 872.3 and REI (SEQ ID NO:8 and 9) light chain amino acid sequences reveals that the residues are identical at positions 46, 58 and 71 but are different at position 48.

Thus changing the human residue to the donor mouse residue at position 48 may further improve the binding characteristics of the CDR-grafted light chain, (B72.3 gL) in accordance with the present invention.

(b) B72.3 Heavy Chain i. Choice of framework

At the outset it was necessary to make a choice of human framework. Simply put, the question was as follows: Was it necessary to use the framework regions from an antibody whose crystal structure was known or could the choice be made on same other criteria?

For B72.3 heavy chain, it was reasoned that, while knowledge of structure was important, transfer of the CDRs from mouse to human frameworks might be facilitated if the overall homology between the donor and receptor frameworks was maximised.

Comparison of the B72.3 heavy chain sequence with those in Kabat (ref. 4) for human heavy chains showed clearly that B72.3 had poor homology for KOL (SEQ ID NO:10) and NEWM (for which crystal structures are available) but was very homologous to the heavy chain for EU.

On this basis, EU was chosen for the CDR-grafting and the following residues transferred as CDRs.

| CDR Number | Residues |
|---|---|
| 1 | 27–36 |
| 2 | 50–63 |
| 3 | 93–102 |

Also it was noticed that the FR4 region of EU was unlike that of any other human (or mouse) antibody. Consequently, in the grafted heavy chain genes this was also changed to produce a "consensus" human sequence. (Preliminary experiments showed that grafted heavy chain genes containing the EU FR4 sequence expressed very poorly in transient expression systems.)

ii. Results with grafted heavy chain genes

Expression of grafted heavy chain genes containing all human framework regions with either gL or cL genes produced a grafted antibody with little ability to bind to mucin. The grafted antibody had about 1% the activity of the chimeric antibody. In these experiments, however, it was noted that the activity of the grafted antibody could be increased to ~10% of B72.3 by exposure to pHs of 2–3.5.

This observation provided a clue as to how the activity of the grafted antibody could be improved without acid treatment. It was postulated that acid exposure brought about the protonation of an acidic residue (pKa of aspartic acid=3.86 and of glutamine acid=4.25) which in turn caused a change in structure of the CDR loops, or allowed better access of antigen.

From comparison of the sequences of B72.3 (ref. 13) and EU (refs. 4 and 5), it was clear that, in going from the mouse to human frameworks, only two positions had been changed in such a way that acidic residues had been introduced. These positions are at residues 73 and 81, where K to E and Q to E changes had been made, respectively.

Which of these positions might be important was determined by examining the crystal structure of the KOL antibody. In KOL heavy chain (SEQ ID NO:10), position 81 is far removed from either of the CDR loops.

Position 73, however, is close to both CDRs 1 and 3 of the heavy chain and, in this position it was possible to envisage that a K to E change in this region could have a detrimental effect on antigen binding.

iii. Framework changes in B72.3 gH gene

On the basis of the above analysis, E73 was mutated to a lysine (K). It was found that this change had a dramatic effect on the ability of the grafted Ab to bind to mucin. Further the ability of the grafted B72.3 produced by the mutated gH/gL combination to bind to mucin was similar to that of the B72.3 chimeric antibody.

iv. Other Framework Changes

In the course of the above experiments, other changes were made in the heavy chain framework regions. Within the accuracy of the assays used, none of the changes, either alone or together, appeared beneficial.

V. Other

All assays used measured the ability of the grafted Ab to bind to mucin and, as a whole, indicated that the single framework change at position 73 is sufficient to generate an antibody with similar binding properties to B72.3.

Comparison of the B72.3 murine and EU heavy chain sequences reveals that the m use and human residues are identical at positions 23, 24, 71 and 78.

Thus the mutated CDR-grafted B72.3 heavy chain corresponds to a preferred embodiment of the present invention.

EXAMPLE 4

CDR-Growing of a Murine Anti-ICAM-1 Monoclonal Antibody

A murine antibody, R6-5-D6 (EP 0314863) having specificity for Intercellular Adhesion Molecule 1 (ICAM-1) was CDR-grafted substantially as described above in previous examples. This work is described in greater detail in co-pending application, British Patent Application No. 9009549.8, the disclosure of which is incorporated herein by reference.

The human EU framework was used as the acceptor framework for both heavy and light chains. The CDR-grafted antibody currently of choice is provided by co-expression of grafted light chain gL221A (SEQ ID NO:26) and grafted heavy chain gH341D (SEQ ID NO:16) which has a binding affinity for ICAM 1 of about 75% of that of the corresponding mouse-human chimeric antibody.

Light Chain gL221A has marine CDRs at positions 24–34 (CDR1), 50–56 (CDR2) and 89–97 (CDR3). In addition several framework residues are also the murine amino acid. These residues were chosen after consideration of the possible contribution of these residues to domain packing and stability of the conformation of the antigen binding region. The residues which have been retained as mouse are at positions 2, 3, 48 (?), 60, 84, 85 and 87.

Comparison of the murine anti-ICAM 1 and human EU light chain amino acid sequences reveals that the murine and human residues are identical at positions 46, 58 and 71.

Heavy Chain gH341D has marine CDRs at positions 26–35 (CDR1), 50–56 (CDR2) and 94–100B (CDR3). In addition murine residues were used in gH341D at positions 24, 48, 69, 71, 73, 80, 88 and 91. Comparison of the marine anti-ICAM 1 and human EU heavy chain amino acid sequences are identical at positions 23, 49 and 78.

EXAMPLE 5

CDR-Grafting of Murine Anti-TNFa Antibodies

A number of murine anti-TNFa monoclonal antibodies were CDR-grafted substantially as described above in previous examples. These antibodies include the murine monoclonal antibodies designated 61 E71, hTNF1, hTNF3 and 101.4 A brief summary of the CDR-grafting of each of these antibodies is given below.

61E71

A similar analysis as described above (Example 1, Section 12.1.) was done for 61E71 and for the heavy chain 10 residues were identified at 23, 24, 48, 49, 68, 69, 71, 73, 75 and 88 as residues to potentially retain as murine. The human frameworks chosen for CDR-grafting of this antibody, and the hTNF3 and 101.4 antibodies were RE1 for the light chain and KOL for the heavy chain.

Three genes were built, the first of which contained 23, 24, 48, 49, 71 and 73 [gH341(6)] as murine residues. The second gene also had 75 and 88 as murine residues [gH341(8)] while the third gene additionally had 68, 69, 75 and 88 as murine residues [gH341(10)]. Each was co-expressed with gL221, the minimum grafted light chain (CDRs only). The gL221/gH341(6) and gL221/gH341(8) antibodies both bound as well to TNF as murine 61E71. The gL221/gH341 (10) antibody did not express and this combination was not taken further.

Subsequently the gL221/gH341(6) antibody was assessed in an L929 cell competition assay in which the antibody competes against the TNF receptor on L929 cells for binding to TNP in solution. In this assay the gL221/gH341(6) antibody was approximately 10% as active as murine 61E71.

hTNF1 hTNF1 is a monoclonal antibody which recognises an epitope on human TNF-. The EU human framework was used for CDR-grafting of both the heavy and light variable domains.

Heavy Chain

In the CDR-grafted heavy chain (ghTNF1) mouse CDRs were used at positions 26–35 (CDR1), 50–65 (CDR2) and 95–102 (CDR3). Mouse residues were also used in the frameworks at positions 48, 67, 69, 71, 73, 76, 89, 91, 94 and 108. Comparison of the TNF1 mouse and EU human heavy chain residues reveals that these are identical at positions 23, 24, 29 and 78.

Light Chain

In the CDR-grafted light chain (gLhTNF1) mouse CDRs were used at positions 24–34 (CDR1), 50–56 (CDR2) and 89–97 (CDR3). In addition mouse residues were used in the frameworks at positions 3, 42, 48, 49, 83, 106 and 108. Comparison of the hTNF1 mouse and BU human light chain residues reveals that these are identical at positions 46, 58 and 71.

The grafted hTNF1 heavy chain was co-expressed with the chimeric light chain and the binding ability of the product compared with that of the chimeric light chain/chimeric heavy chain product in a TNF binding assay. The grafted heavy chain product appeared to have binding ability for TNF slightly better than the fully chimeric product.

Similarly, a grafted heavy chain/grafted light chain product was co-expressed and compared with the fully chimeric product and found to have closely similar binding properties to the latter product.

hTNP3 hTNF3 recognises an epitope on human TNP-α. The sequence of hTNF3 shows only 21 differences compared to 61E71 in the light and heavy chain variable regions, 10 in the light chain (2 in the CDRs at positions 50, 96 and 8 in the framework at 1, 19, 40, 45, 46, 76, 103 and 106) and 11 in the heavy chain (3 in the CDR regions at positions 52, 60 and 95 and 8 in the framework at 1, 10, 38, 40, 67, 73, 87 and 105). The light and heavy chains of the 61E71 and hTNF3 chimeric antibodies can be exchanged without loss of activity in the direct binding assay. However 61E71 is an order of magnitude less able to compete with the TNF receptor on L929 cells for TNF-a compared to hTNF3. Based on the 61E71 CDR grafting data gL221 and gH341 (+23, 24, 48, 49 71 and 73 as mouse) genes have been built for hTNF3 and tested and the resultant grafted antibody binds well to TNF-a, but competes very poorly in the L929 assay. It is possible that in this case also the framework residues identified for OKT3 programme may improve the competitive binding ability of this antibody.

101.4

101.4 is a further murine monoclonal antibody able to recognize human TNF-a. The heavy chain of this antibody shows good homology to KOL and so the CDR-grafting has been based on RE1 for the light chain and KOL for the heavy chain. Several grafted heavy chain genes have been constructed with conservative choices for the CDR's (gH341) (SEQ ID NO:11) and which have one or a small number of non-CDR residues at positions 73, 78 or 77–79 inclusive, as the mouse amino acids. These have been co-expressed with cL or gL221. In all cases binding to TNF equivalent to the chimeric antibody is seen and when co-expressed with cL the resultant antibodies are able to compete well in the L929 assay. However, with gL221 the resultant antibodies are at least an order of magnitude less able to compete for TNF against the TNF receptor on L929 cells.

Mouse residues at other positions in the heavy chain, for example, at 23 and 24 together or at 76 have been demonstrated to provide no improvement to the competitive ability of the grafted antibody in the L929 assay.

A number of other antibodies including antibodies having specificity for interleukins e.g. IL1 and cancer markers such as carcinoembryonic antigen (CEA) e.g. the monoclonal antibody A5B7 (ref. 21), have been successfully CDR-grafted according to the present invention.

It will be appreciated that the foregoing examples are given by way of illustration only and are not intended to limit the scope of the claimed invention. Changes and modifications may be made to the methods described whilst still falling within the spirit and scope of the invention.

REFERENCES

1. Kohler & Milstein, Nature, 265, 295–497, 1975.
2. Chatenoud et al, (1986), J. Immunol. 137, 830–838.
3. Jeffers et al, (1986), Transplantation, 41, 572–578.
4. Begent et al, Br. J. Cancer 62: 487 (1990).
5. Verhoeyen et al, Science, 239, 1534–1536, 1988.
6. Riechmann et al, Nature, 332, 323–324, 1988.
7. Kabat, E. A., Wu, T. T., Reid-Miller, M., Perry, H. M., Gottesman, K. S., 1987, in Sequences of Proteins of Immunological Interest, US Department of Health and Human Services, NIH, USA.
8. Wu, T. T., and Kabat, E. A., 1970, J. Exp. Med. 132 211–250.
9. Queen et al, (1989), Proc. Natl. Acad. Sci. USA, 86, 10029–10033 and WO 90/07861
10. Maniatis et al, Molecular Cloning, Cold Spring Harbor, New York, 1989.
11. Primrose and Old, Principles of Gene Manipulation, Blackwell, Oxford, 1980.
12. Sanger, F., Nicklen, S., Coulson, A. R., 1977, Proc. Natl. Acad. Sci. USA, 74 5463
13. Kramer, W., Drutsa, V., Janasen, H.-W., Kramer, B., Plugfelder, M., Fritz, H.-J., 1984, Nucl. Acids Res. 12, 9441
14. Whittle, N., Adair, J., Lloyd, J. C., Jenkins, E., Devine, J., Schlom, J., Raubitshek, A., Colcher, D., Bodmer, M., 1987, Protein Engineering 1, 499.
15. Sikder, S. S., Akolkar, P. N., Kaledas, P. M., Morrison, S. L., Kabat, E. A., 1985, J. Immunol. 135, 4215.
16. Wallick, S. C., Kabat, E. A., Morrison, S. L., 1988, J. Exp. Med. 168, 1099
17. Bebbington, C. R., Published International Patent Application WO 89/01036.
18. Granthan and Perrin 1986, Immunology Today 7, 160.
19. Kozak, M., 1987, J. Mol. Biol. 196, 947.
20. Jones, T. P., Dear, P. H., Foote, J., Neuberger, M. S., Winter, G., 1986, Nature, 321, 522
21. Harwood et al, Br. J. Cancer, 54, 75–82 (1986).

What is claimed is:

1. A process for producing a CDR-grafted antibody comprising:
   a) producing an expression vector having a nucleic acid sequence encoding an antibody molecule having affinity for a predetermined antigen and comprising a composite heavy chain and a complementary light chain, said composite heavy chain having a variable domain including complementarity determining regions (CDRs) and framework regions, wherein said framework regions of said variable domain comprise predominantly human acceptor antibody heavy chain framework region residues, the remaining heavy chain framework region residues corresponding to the equivalent residues in a donor antibody having affinity for said predetermined antigen, wherein, according to the Kabat numbering system, in said composite heavy chain, said CDRs comprise donor residues at residues 31 to 35, 50 to 58, and 95 to 102; and said framework regions comprise donor residues at amino acid residues 6, 24, 48, 49, 71, 73, and 78; or
   b) producing a first expression vector having a nucleic acid sequence encoding an antibody molecule having affinity for a predetermined antigen and comprising a composite heavy chain, said composite heavy chain having a variable domain including complementarity determining regions (CDRs) and framework regions, wherein said framework regions of said variable domain comprise predominantly human acceptor antibody heavy chain framework region residues, the remaining heavy chain framework region residues corresponding to the equivalent residues in a donor antibody having affinity for said predetermined antigen, wherein, according to the Kabat numbering system, in said composite heavy chain: said CDRs comprise donor residues at residues 31 to 35, 50 to 58, and 95 to 102; and said framework regions comprise donor residues at amino acid residues 6, 24, 48, 49, 71, 73, and 78 and producing second expression vector having a nucleic acid encoding said complementary antibody light chain;

c) transforming a host cell with the or each vector;
d) culturing the transfected host cell; and
e) recovering the CDR-grafted antibody.

2. The process of claim 1, wherein a residue selected from the group consisting of residues 1, 3, and 76 in said composite heavy chain are additionally donor residues.

3. The process of claim 1, wherein a residue selected from the group consisting of residues 36, 94, 104, 106, and 107 in said composite heavy chain are additionally donor residues.

4. The process of claim 3, wherein a residue selected from the group consisting of residues 2, 4, 38, 46, 67, and 69 in said composite heavy chain are additionally donor residues.

5. The process of claim 1, wherein amino acid residues 26 to 30 and 59 to 65 in said composite heavy chain are additionally donor residues.

6. The process of claim 1, wherein said complementary light chain is a composite light chain having a variable domain including complementarity determining regions (CDRs) and framework regions, wherein said framework regions of said variable domain comprise predominantly human acceptor antibody light chain framework region residues, the remaining light chain framework region residues corresponding to the equivalent residues in a donor antibody having affinity for said predetermined antigen, wherein, according to the Kabat numbering system, in said composite light chain, said CDRs comprise donor residues at least at residues 24 to 34, 50 to 56, and 89 to 97; and amino acids residues 46, 48, 58, and 71 at least are donor residues.

7. The process of claim 6, wherein amino acid residues 1, 3, 60 (if this residue can form a salt bridge with residue 54), and 70 (if this residue can form a salt bridge with residue 24) in said composite light chain are additionally donor residues.

* * * * *